US012667662B2

(12) United States Patent
Srinivasan et al.

(10) Patent No.: US 12,667,662 B2
(45) Date of Patent: *Jun. 30, 2026

(54) SMART MEDICATION DELIVERY DEVICES FOR PROVIDING USERS WITH DELIVERY INFOMATICS AND METHODS OF USING SAME

(71) Applicant: INSULET CORPORATION, Acton, MA (US)

(72) Inventors: Sudarsan Srinivasan, North Brunswick, NJ (US); Michel Bruehwiler, Newton, MA (US); Tyson Montidoro, Davie, FL (US); Mohammadreza Ramezanifard, San Diego, CA (US); Cole Constantineau, Cambridge, MA (US); Jeffrey Chagnon, Somerville, MA (US); Stefan Gisler, Winterthur (CH)

(73) Assignee: INSULET CORPORATION, Acton, MA (US)

( * ) Notice: Subject to any disclaimer, the term of this patent is extended or adjusted under 35 U.S.C. 154(b) by 497 days.

This patent is subject to a terminal disclaimer.

(21) Appl. No.: 18/321,038

(22) Filed: May 22, 2023

(65) Prior Publication Data
US 2023/0372611 A1 Nov. 23, 2023

Related U.S. Application Data

(63) Continuation of application No. 16/095,787, filed as application No. PCT/US2017/029613 on Apr. 26, 2017, now Pat. No. 11,666,701.
(Continued)

(51) Int. Cl.
*A61M 5/168* (2006.01)
*A61M 5/142* (2006.01)
(Continued)

(52) U.S. Cl.
CPC .... *A61M 5/16831* (2013.01); *A61M 5/14248* (2013.01); *A61M 5/172* (2013.01);
(Continued)

(58) Field of Classification Search
CPC .......... A61M 5/20; A61M 5/14; A61M 5/168; A61M 5/172; A61M 5/16831;
(Continued)

(56) References Cited

U.S. PATENT DOCUMENTS

| | | | |
|---|---|---|---|
| 8,432,260 B2 | 4/2013 | Talty et al. | |
| 8,449,523 B2 | 5/2013 | Brukalo et al. | |

(Continued)

FOREIGN PATENT DOCUMENTS

WO 20140152704 A1 9/2014

OTHER PUBLICATIONS

Extended European Search Report dated Oct. 1, 2019, which issued in the corresponding European Patent Application No. 17790335.8.
(Continued)

*Primary Examiner* — Courtney B Fredrickson
*Assistant Examiner* — Anna E Vargas
(74) *Attorney, Agent, or Firm* — Goodwin Procter LLP

(57) ABSTRACT
A medication delivery device (MDD) (e.g., injection pen, wearable pump) is paired with an external device (e.g., smart phone, iPad, computer) via wireless link or wireline connection. The MDD provides to the external device captured data from the flow sensor relating to medicine delivery to a patient to ensure complete delivery and minimize MDD misuse or malfunction or inaccuracies in dosing. The MDD can have Bluetooth™ and/or near field communication (NFC) communication circuits for proximity-based pairing and connectivity with the external device for real-time or deferred transfer of captured data to the external device, depending on memory and power availability at the MDD.
(Continued)

SMART DEVICE

100

The MDD or external device can use captured data and corresponding time stamps to determine flow infomatics such as flow rate, total dose delivered, and dose completion status. An LED on the MDD indicates states such as powered on, paired, delivery in progress and delivery completion.

20 Claims, 17 Drawing Sheets

Related U.S. Application Data

(60) Provisional application No. 62/328,714, filed on Apr. 28, 2016.

(51) Int. Cl.

| | |
|---|---|
| *A61M 5/172* | (2006.01) |
| *A61M 5/20* | (2006.01) |
| *H04B 5/70* | (2024.01) |

(52) U.S. Cl.
CPC ....... *A61M 5/20* (2013.01); *A61M 2205/0244* (2013.01); *A61M 2205/18* (2013.01); *A61M 2205/3327* (2013.01); *A61M 2205/3331* (2013.01); *A61M 2205/3334* (2013.01); *A61M 2205/3368* (2013.01); *A61M 2205/3561* (2013.01); *A61M 2205/3584* (2013.01); *A61M 2205/50* (2013.01); *A61M 2205/52* (2013.01); *A61M 2205/587* (2013.01); *H04B 5/70* (2024.01)

(58) Field of Classification Search
CPC .......... A61M 5/16877; A61M 2205/50; A61M 2205/52; A61M 2205/3584; A61M 2005/206; G06F 19/30; H04B 5/0025
See application file for complete search history.

(56) References Cited

U.S. PATENT DOCUMENTS

| | | | |
|---|---|---|---|
| 8,617,127 B2 * | 12/2013 | Woolston | A61M 5/24 |
| | | | 604/246 |
| 11,666,701 B2 | 6/2023 | Srinivasan et al. | |
| 2011/0306882 A1 | 12/2011 | Hannon et al. | |
| 2013/0177455 A1 | 7/2013 | Kamen et al. | |
| 2013/0329860 A1 | 12/2013 | Nonaka | |
| 2014/0107585 A1 | 4/2014 | Eggert et al. | |
| 2015/0126963 A1 | 5/2015 | Despa et al. | |
| 2015/0279186 A1 | 10/2015 | Chen et al. | |
| 2015/0290396 A1 | 10/2015 | Nagar et al. | |
| 2016/0012205 A1 | 1/2016 | Saint et al. | |
| 2016/0030683 A1 * | 2/2016 | Taylor | A61M 5/345 |
| | | | 604/151 |
| 2016/0074587 A1 | 3/2016 | Searle et al. | |
| 2016/0259913 A1 | 9/2016 | Yu et al. | |
| 2016/0302726 A1 | 10/2016 | Chang | |
| 2017/0068799 A1 | 3/2017 | Mensinger et al. | |
| 2017/0132392 A1 | 5/2017 | Gerken | |
| 2017/0182256 A1 | 6/2017 | Andersen et al. | |
| 2017/0203030 A1 | 7/2017 | Brewer et al. | |
| 2018/0296767 A1 | 10/2018 | Sall | |

OTHER PUBLICATIONS

International Search Report dated Jul. 6, 2017, which issued in corresponding PCT Patent Application PCT/US2017/029613.

* cited by examiner

- DATA TRANSFER (WHEN?, HOW?)

- WIRELESS COMMUNICATION/WIRED CONNECTIVITY

- DEVICE PAIRING

- TIME RECORDING DEVICE

- HOW CLOSE DO THE PLATFORMS NEED TO BE FOR DATA TRANSFER?

OR

PROXIMITY

101

DATA CAN TRANSFER DURING INJECTION

DOSE HISTORY DOWNLOAD CAN OCCUR AT ANY TIME 10 cm PAIRING 10 m DATA TRANSFER

PROXIMITY

SMART DEVICE

SMART MEDICATION DELIVERY DEVICES FOR PROVIDING USERS WITH DELIVERY INFOMATICS AND METHODS OF USING SAME

RELATED APPLICATION(S)

This application is a continuation patent application of U.S. application Ser. No. 16/095,787, filed Oct. 23, 2018, now U.S. Pat. No. 11,666,701, which is a U.S. national stage entry of PCT International Application No. PCT/US2017/029613, filed Apr. 26, 2017, which claims priority to and the benefit of U.S. Provisional Application No. 62/328,714, filed Apr. 28, 2016, each of which are incorporated herein by reference in their entireties.

FIELD OF THE INVENTION

Various illustrative embodiments of the invention relate to smart delivery devices (e.g., medication pens, wearable pumps, wearable patches with delivery ports for use with syringe or medication pen) that sense and provide medication delivery infomatics (e.g., medication delivery flow, delivery completion status, time of delivery, and so on) to users.

BACKGROUND OF THE INVENTION

Medication pens are typically used to inject medication into a patient. A person who must periodically self-inject doses of medication will typically carry a medication pen and several single-use pen needles. A medication pen is designed for safety and sterility. However, inefficiencies and inconveniences arise, as well as inaccuracies in dosing such as from misuse or malfunctioning of the medication pen. A need exists for an improved medication pen that can provide a user with more accurate information regarding delivered dose and adherence to a prescribed medication dosage regimen.

SUMMARY OF THE INVENTION

It is an aspect of illustrative embodiments of the present invention to provide a medication delivery device comprising a sensor configured to sense flow of medication from a medication delivery device (MDD) to patient; a processing device configured to receive sensor data from the sensor; and a wireless communication circuit configured to transmit the sensor data from the MDD to an external device on a wireless link; wherein the processing device is configured to control pairing of the MDD to an external device and, once the external device is paired with the MDD, to transmit the sensor data to the external device via the wireless link.

For example, in accordance with an aspect of the present invention, the processing device is configured, when the external device is paired with the MDD, to transmit the sensor data to the external device via the wireless link during delivery of the medication to the patient.

In accordance with aspects of illustrative embodiments of the present invention, the medication delivery device is at least one of a medicine injection pen, a pen needle, a pen needle attachment, a medicine delivery pump, wearable pump, and a patch pump. The sensor is at least one of a flow sensor, a thermal flow sensor, a pressure sensor, and a Micro-Electro-Mechanical System (MEMS) sensor. The external device can be at least one of a mobile phone, a laptop, an iPad, and a processing device having an integral or connected communications interface.

In accordance with aspects of illustrative embodiments of the present invention, the MDD comprises a power source and a switch that, when activated, supplies power from the power source to at least the processor device and the sensor. The processing device is configured actuate the switch to terminate supply of power from the power source to at least one of the processing device, the sensor and the wireless communication circuit after either of the MDD and external device failing to pair within a designated time period after initiation of pairing, and the sensor failing to sense a designated flow threshold within a designated time period.

In accordance with aspects of illustrative embodiments of the present invention, the sensor data comprises voltage values corresponding to a flow rate of medication delivered to the patient. The MDD or external device provides time stamps to the sensor data based on when the sensor data is received and stores the sensor data and corresponding time stamps. The external device can be configured to determine at least one of flow rate of the delivery of the medication to the patient over time, and total delivered amount of medication delivered to the patient during a designated period of time, using the sensor data and the time stamps.

In accordance with aspects of illustrative embodiments of the present invention, the pairing can be at least one of establishing a wireless communication link between the MDD and the external device, and establishing a wireline connection between the MDD and the external device for communication.

In accordance with aspects of illustrative embodiments of the present invention, the MDD further comprises an indicator, and the processing device is configured to control the indicator to indicate that the MDD is powered on and initiating pairing with the external device. For example, the processing device is configured to control the indicator to indicate other states of the MDD selected from the group consisting of a state in which the MDD is paired with the external device, a state in which flow of medication from the MDD to the patient is in progress, a state in which the MDD is paired with the external device and flow of medication from the MDD to the patient is in progress, and a state in which delivery of the medication to the patient is complete. For example, the processing device controls the indicator to indicate the state in which delivery of the medication to the patient is complete when the sensor data from the sensor corresponds to a designated minimum flow rate.

In accordance with aspects of illustrative embodiments of the present invention, the MDD further comprises a time clock and a memory device, and the processing device is configured to store sensor data and corresponding time stamps obtained via the time clock. For example, the processing device is configured, when the external device is paired with the MDD, to transmit the sensor data to the external device via the wireless link, the transmission of data occurring either during real-time data capture by the sensor while medication is delivered to the patient, and after data capture by the sensor.

In accordance with aspects of illustrative embodiments of the present invention, the wireless communication circuit and the processing device are implemented in a near-field communication (NFC) integrated circuit chip, the external device is NFC-enabled, and the NFC chip is operable to establish the wireless link between the MDD and the external device as a NFC link. The NFC chip has a memory for storing the sensor data and corresponding time stamps from a clock in the MDD, and the sensor data and time stamps are downloaded to the external device when the MDD is scanned by the external device. The NFC chip can be powered from the scanning by the external device.

In accordance with aspects of illustrative embodiments of the present invention, the MDD further comprises a second wireless communication circuit that establishes a second wireless link between the MDD and the external device that has a greater range than the NFC link, the second wireless communication circuit comprising a memory for storing the sensor data and the corresponding time stamps from the clock in the MDD. For example, the second wireless communication circuit is a Bluetooth™ chip that transmits the captured sensor data during delivery of the medication regardless when proximal to the external device. The NFC chip can enable pairing of the Bluetooth™ chip to the external device which is Bluetooth™-enabled.

Additional and/or other aspects and advantages of the present invention will be set forth in the description that follows, or will be apparent from the description, or may be learned by practice of the invention. The present invention may comprise delivery devices (e.g., pen, pen needle adapter, wearable pump) and/or connected smart devices (e.g., mobile phone or computer with smart delivery app) and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above aspects and features of the present invention will be more apparent from the description for the illustrative embodiments of the present invention taken with reference to the accompanying drawings, in which.

Throughout the drawing figures, like reference numbers will be understood to refer to like elements, features and structures.

DETAILED DESCRIPTION OF ILLUSTRATIVE EMBODIMENTS

Figure 1A:
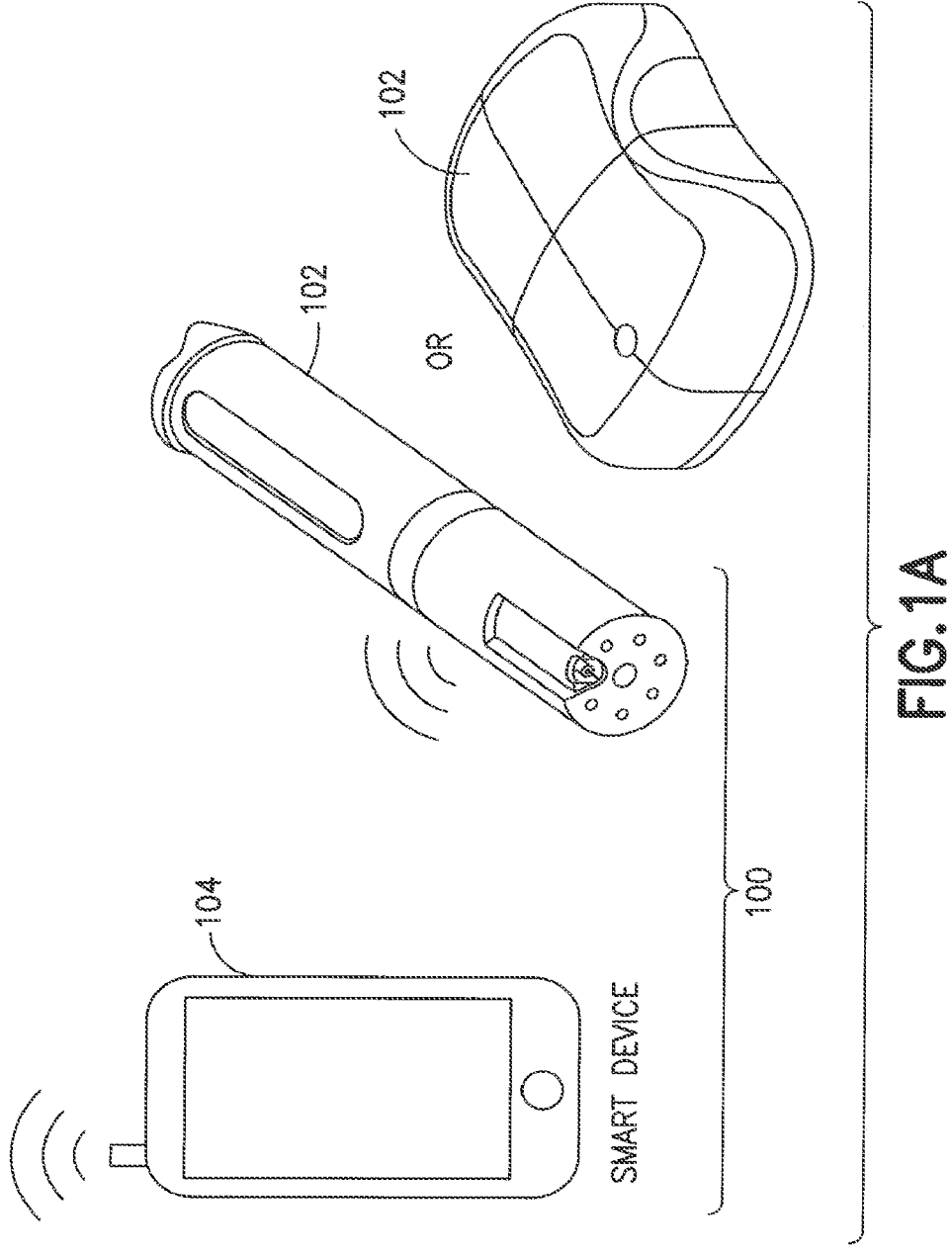
FIG. 1A depicts communicating platforms in a smart delivery system in accordance with an illustrative embodiment of the present invention.

Reference will now be made in detail to embodiments of the present invention, which are depicted in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

In accordance with illustrative embodiments of the present invention, a medication delivery device is configured to sense data related to medication delivery and to communicate sensed delivery data or dose capture data to an external device. Dose capture at the time of delivery represents advantages over existing delivery systems that do not capture dose information at all, or do so in a limited manner and not immediately/concurrently with dose delivery. For example, a conventional medication delivery pen employs a dial by which a user enters a prescribed amount of medication to be delivered. The pen is configured to deliver an amount of medication that corresponds to the dialed input; however, the pen has no means by which to confirm that the prescribed amount of medication was actually delivered. For example, if the medication delivery pen is malfunctioning or misused, a user may not realize that he or she is not receiving the prescribed amount. For example, a user may not hold the pen needle long enough to complete the prescribed delivery, or may misuse device and cause a leak, thereby preventing administration of full dose as prescribed.

FIG. 1A depicts a smart delivery system 100 comprises two communicating platforms, that is, a delivery device 102 and another connected device 104. The delivery device 102 is connected wirelessly or via a wireline connection to the other connected device 104. The delivery device 102 delivers fluid such as a medicine (e.g., insulin) to a user. The delivery device 102 can be, for example, a medicine pen, or a pen needle attachment, or a medicine pump such as a patch pump or other wearable pump. The other connected device 104 can be, for example, a mobile phone, laptop, iPad or other processing device.

Figure 1B:
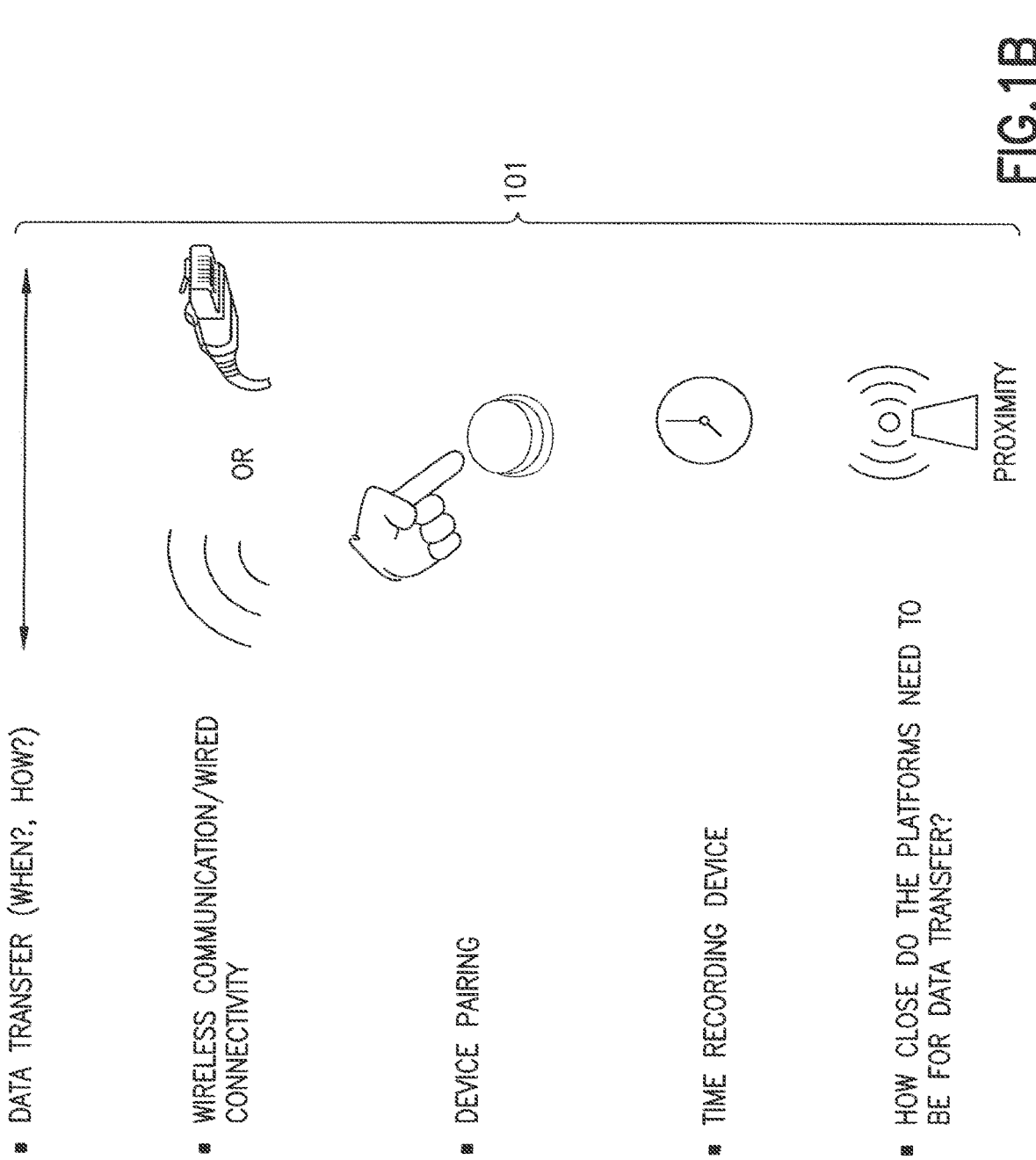
FIG. 1B depict different hardware and software features that impact delivery infomatics in a smart delivery system in accordance with illustrative embodiments of the present invention.

As exemplified in the different embodiments described below in connection with FIGS. 2 through 16, the two communicating platforms, that is, a delivery device 102 and another connected device 104 can have different combinations of hardware and software capabilities or features 101 that impact the delivery infomatics. With reference to FIG. 1B, the data transfer can differ depending on when and how data transfer occurs between a delivery device 102 and its associated other connected device 104. For example, the delivery device 102 can transfer data regarding drug delivery status (e.g., complete or incomplete) or other delivery infomatics (e.g., rate, timing) in real-time (e.g., during injection) or at any time such as after injection when disconnected devices are eventually paired or otherwise connected or scanned. The communication connectivity can be wireless or wired. Different wireless connectivity methods can be used (e.g., Bluetooth™ or WiFi or near field communication (NFC) technology) which can, in turn, impact device pairing if needed and need for proximity of the delivery 102 device to the other connected device 104. For example, Bluetooth™ employs a particular device pairing process. The proximity of the two communicating platforms relative to each other depends on the connectivity method used. For example, the delivery device 102 may need to be within 10 meters of the other device 104 if paired via Bluetooth™ whereas the two communicating platforms 102 and 104 may need to be more proximal to each other (e.g., on the order of 10 centimeters apart or less) for NFC pairing. The timing of data transfer can be impacted depending on whether or not the two communicating platforms 102 and 104 or at least the delivery device 102 has a time recording capability or not.

In accordance with an illustrative embodiment of the present invention described with reference to FIGS. 2, 3 and 4, a direct stream smart delivery system 100 comprises a delivery device 102 connected to another device 104 such as a smart phone via a wireless connection. The particulars of the processing circuit, user interface, cellular communication interface and other wireless communication interface (e.g., WiFi and/or Bluetooth™ and/or NFC) of the smart phone 104 are conventional, and their descriptions are omitted here for conciseness. In accordance with an aspect of illustrative embodiments of the present invention, the smart phone 104 is provided with a delivery infomatics app to connect to and cooperate with the delivery device 102. The user pairs the smart phone 104 with the delivery device 102 for synchronization using, for example, standard Bluetooth™ technology methods.

Figure 2:
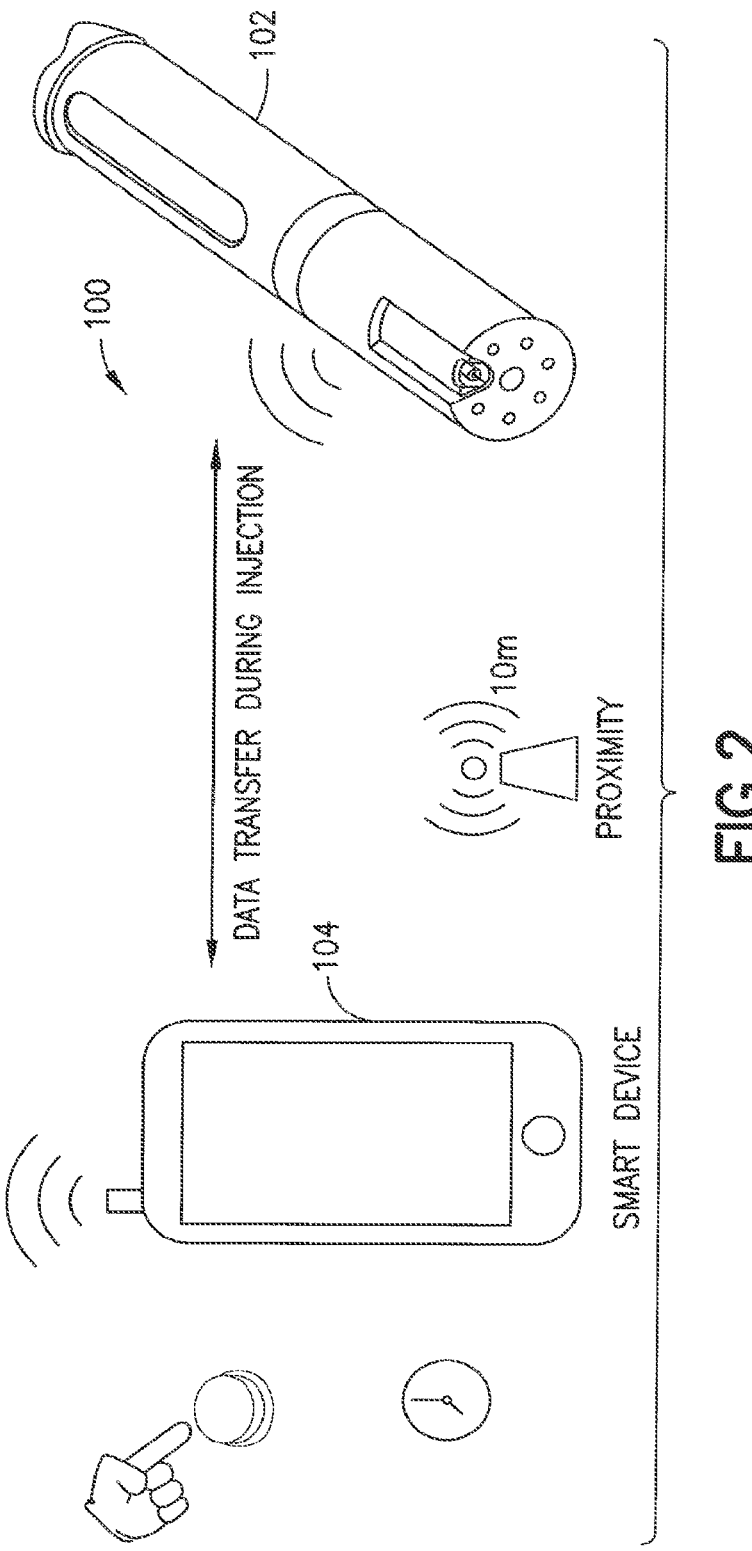
FIG. 2 depicts a direct stream smart delivery system in accordance with an illustrative embodiment of the present invention.

With continued reference to FIG. 2, data synchronization between the delivery device 102 and the smart phone 104 can occur with every injection, for example, to get delivery data. The smart phone 104 advantageously provides time recording capability (e.g., data provided during or immediately after injection from the delivery device 102 is stored at a memory device in the smart phone with a time stamp using a clock in the smart phone). Bluetooth™ connectivity between the smart phone 104 and the delivery device 102 allows the delivery device to be within about 10 meters of the smart phone and operable to transfer delivery data to the smart phone. The pairing with a smart phone 104 for data transfer and use of the smart phone's memory and time recording features allow for electronic components in the delivery device 102 to be minimized for reduced complexity and reduced cost of manufacture.

The delivery device 102 comprises electronics (e.g., electronic components generally indicated at 103 in FIG. 3) provided integrally or via a removable attachment (e.g., a pen needle adapter or other pen attachment) to the delivery device 102. As described below, the electronics 103 generally comprise a processing device, a memory device, a sensor for detecting a fluid (e.g., medicine) delivery characteristic or other delivery-related information, an indicator such as a light emitting diode (LED), and a communications interface. The communications interface is configured to connect the delivery device 102 to the other device 104 and can comprise a wireline connector (e.g., a mini USB) or a wireless interface to communicate for example via Bluetooth™ or WiFi or near field communication (NFC) technology.

Figure 3:
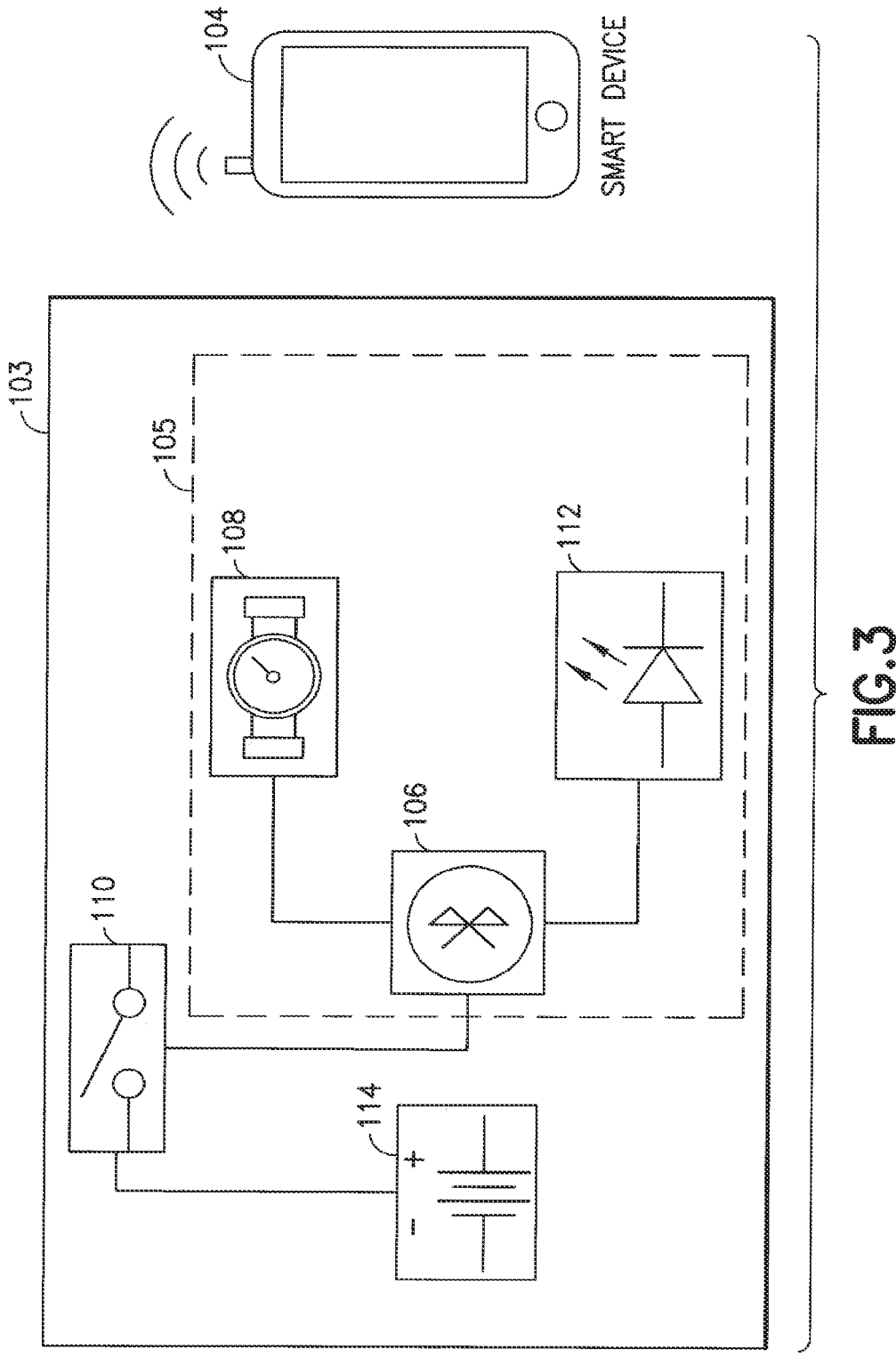
FIG. 3 is a block diagram of some of the components in the smart delivery system of FIG. 2 in accordance with an illustrative embodiment of the present invention.

For example, as shown FIG. 3, the delivery device 102 or an add-on device (e.g., a pen needle adapter) for the delivery device can comprise a Bluetooth™ chip 106 (e.g., Bluetooth™ low energy LE chip such as TI CC 2541 which has an on-board processor and memory for synchronization and other Bluetooth™ operations) that is connected via a switch (e.g., a double-pole double-throw (DPDT) switch) 110 to a power source 114 such as one or more batteries. For example, the power source 114 can be a rechargeable or non-rechargeable lithium battery and can be bendable depending on the form factors of the delivery device 102. As a further example, the power source 114 can be a thin-film lithium battery or plural parallel connected batteries, or a coin cell battery. The delivery device 102 has a sensor 108 such as a Sensirion flow meter (e.g., LPG10 or equivalent) for detecting flow infomatics of delivered fluid or medication (e.g., flow rate). Other types of sensors for detecting characteristics of the delivery of a fluid by the delivery device 102 can be used. The Bluetooth™ chip is configured to receive data from the sensor and transfer it to paired device such as the smart phone 104. The delivery device 102 can also be provided with one or more indicators 112 such as LEDs described below in connection with FIG. 4.

The cooperation of the delivery device 102 and the other connected device 104 in a direct stream smart delivery system 100 as depicted in FIG. 2 will be described with reference to a medicine pen and a smart phone, for example. It is to be understood that the delivery device 102 can be a different device such as a wearable pump or patch pump, and the other connected device 104 can be a smart phone or a different device such as a laptop iPad or other portable processing device with wireless connectivity to a delivery device. With reference to FIG. 4, a user can remove a cap on the pen 102 and pull a dial thereon downwards or otherwise configure the pen for medication delivery (block 120). The delivery device 102 is configured such that user initiation of medication delivery (e.g., dialing a pen or pressing a button on a pump) causes the switch to close to allow supply of power to the flow sensing system (e.g., components indicated generally at 105 in FIG. 3) comprising the processor (e.g., in the Bluetooth™ chip 106), flow sensor 108 and indicator(s) 112 (block 122). Upon initial powering of the Bluetooth™ chip, the chip can be configured to drive an LED 112 to indicate a first state, that is, the flow sensor 108 is powered on but the delivery device 102 is not yet paired with the smart phone 104 (block 124). The Bluetooth™ chip 106 in the delivery device 102 is configured to commence advertising to pair with the smart phone 104 (block 126). If no pairing occurs, the flow sensing system 105 is powered off (e.g., the DPDT is opened in response to an output from the Bluetooth™ chip) (block 128).

Figure 4:
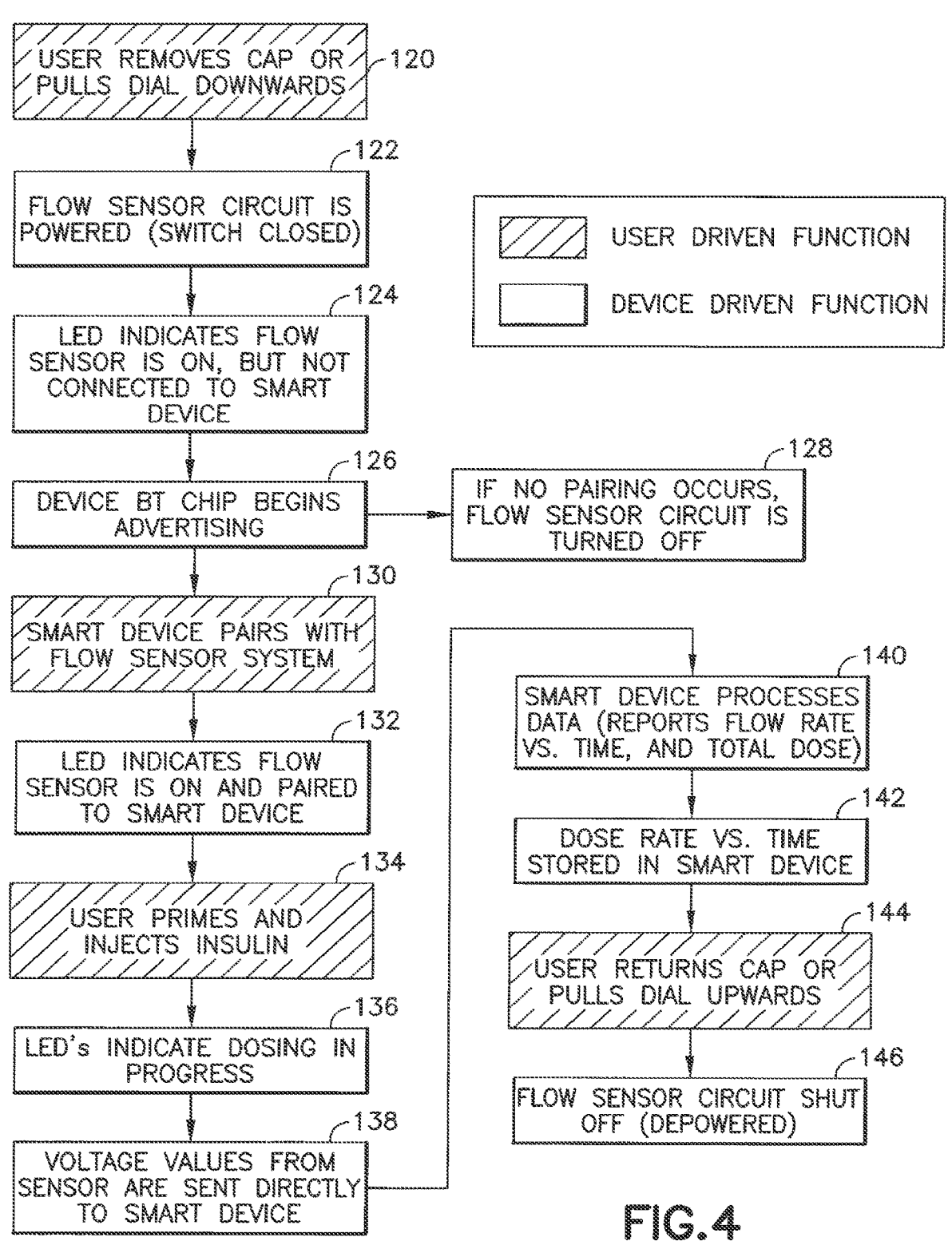
FIG. 4 is a flow chart depicting operations in the smart delivery system of FIG. 2 in accordance with an illustrative embodiment of the present invention.

With continued reference to FIG. 4, if pairing is successful between the smart phone 104 and the flow sensing system 105 (block 130), voltage values from the sensor 108 can be sent directly to the smart phone (block 138). The user can then prime the pen 102 and inject the medication (block 134). An LED 112 on the delivery device 102 is driven to indicate a second state, that is, pairing is complete and delivery or dosing is in progress (block 136). The flow sensor sends sensed delivery data during delivery to the paired smart phone 104 via Bluetooth™. While dosing is in progress, the smart phone 104 can be configured by the delivery infomatics app to process received delivery data to determine, for example, flow rate over time and total dose (block 140). The device 102, for example, can capture time of dose and send timing information with flow and total amount delivered data to smart phone 104. The time of dose can alternatively be provided by the smart phone 104 as it receives dose information from the device 102. Either way, the dose rate versus time can be stored in the smart phone (block 142). The user returns the cap to the pen or pulls the pen dose dial upwards or otherwise operates the pen to return to a non-dosing operational state (block 144), and the flow sensing system 105 is then powered off (block 146).

With further reference to the LED 112, one or more LEDs can be provided on the delivery device to show one or more states. For example, the LED(s) can indicate one or more of the following states: (1) the delivery device 102 is powered and advertising (e.g., both operations can happen at the same time and, if a time limit is expired, the device is powered off); (2) the device 102 is paired with a smart phone 104 or other connected device; (3) insulin or other medicine is flowing through a cannula or other pathway in the delivery device 102 to the patient; and/or (4) the patient or other user may remove the cannula from delivery site. This is an extremely important benefit of the LED(s) 112. Typical injection pen user instructions tell users to deliver the prescribed dose and then count to 10, which presents only a very subjective and likely erroneous 'delivery' indication. The delivery device 102, by contrast, is configured for delivering a dose, sensing when the dosing is finished (e.g., flowrate=0), and then operating a countdown timer that alerts the user when it is safe to remove the device from the delivery site. In addition, a single LED can be used to indicate multiple states such as all four of the previously mentioned states. For example, an RGB LED can indicate different colors that may correspond to device states, and may flash in different manners as well depending on delivery status or delivery device state.

The smart delivery system 100 employing a direct stream as illustrated in FIGS. 2, 3 and 4 is advantageous because the processing device 106 can get flow data from the sensor 108 during dosing (e.g., data such as how much time is needed to deliver the desired dose, total dose delivered, dose time, dose rate, or dose status such as "in progress" or "complete"). For example, flow rate data during delivery can indicate issues such as clogging and allows user alerts to be generated during dosing.

Figure 5:
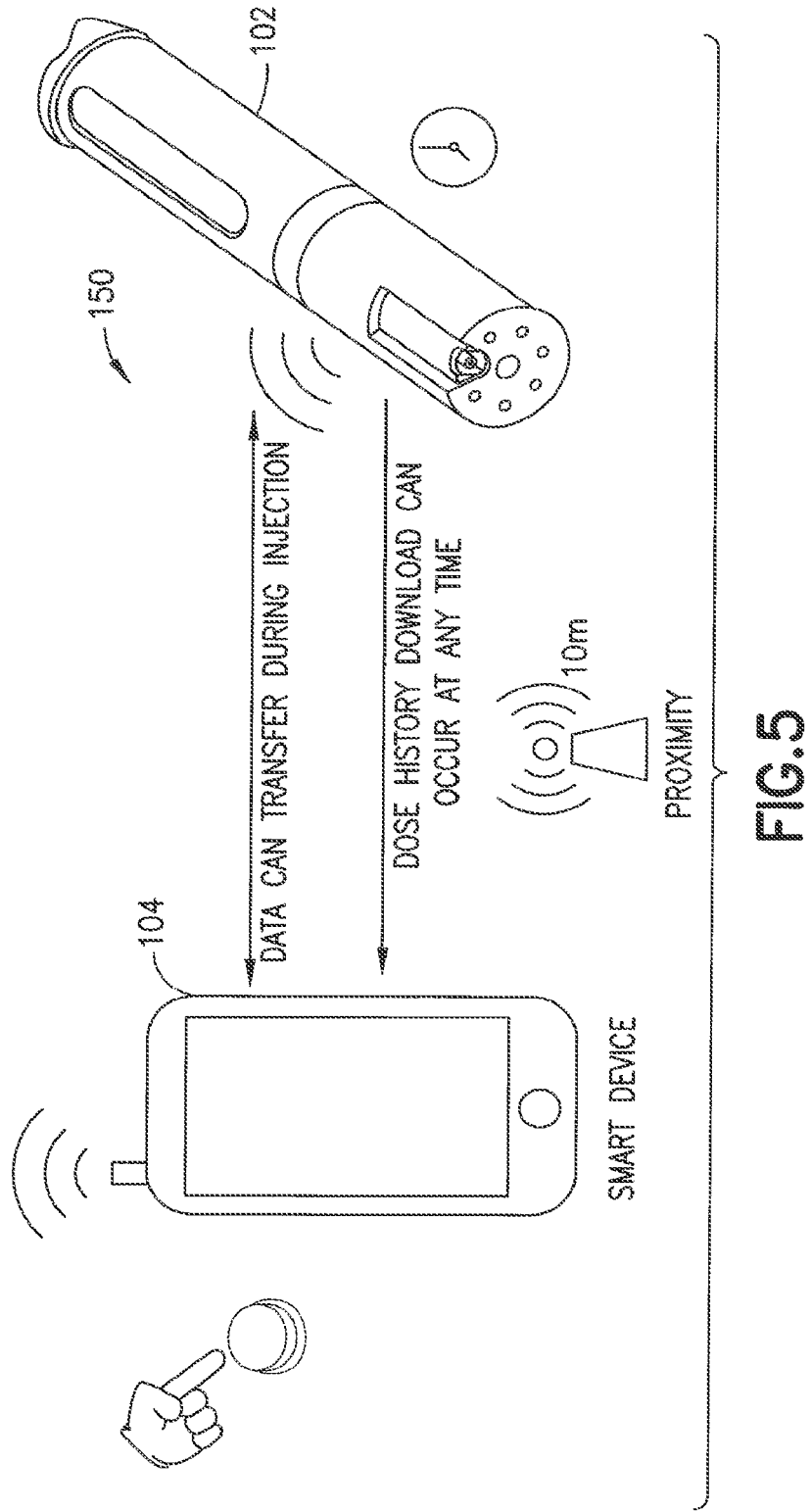
FIG. 5 depicts a memory-based smart delivery system in accordance with an illustrative embodiment of the present invention.
Figure 6:
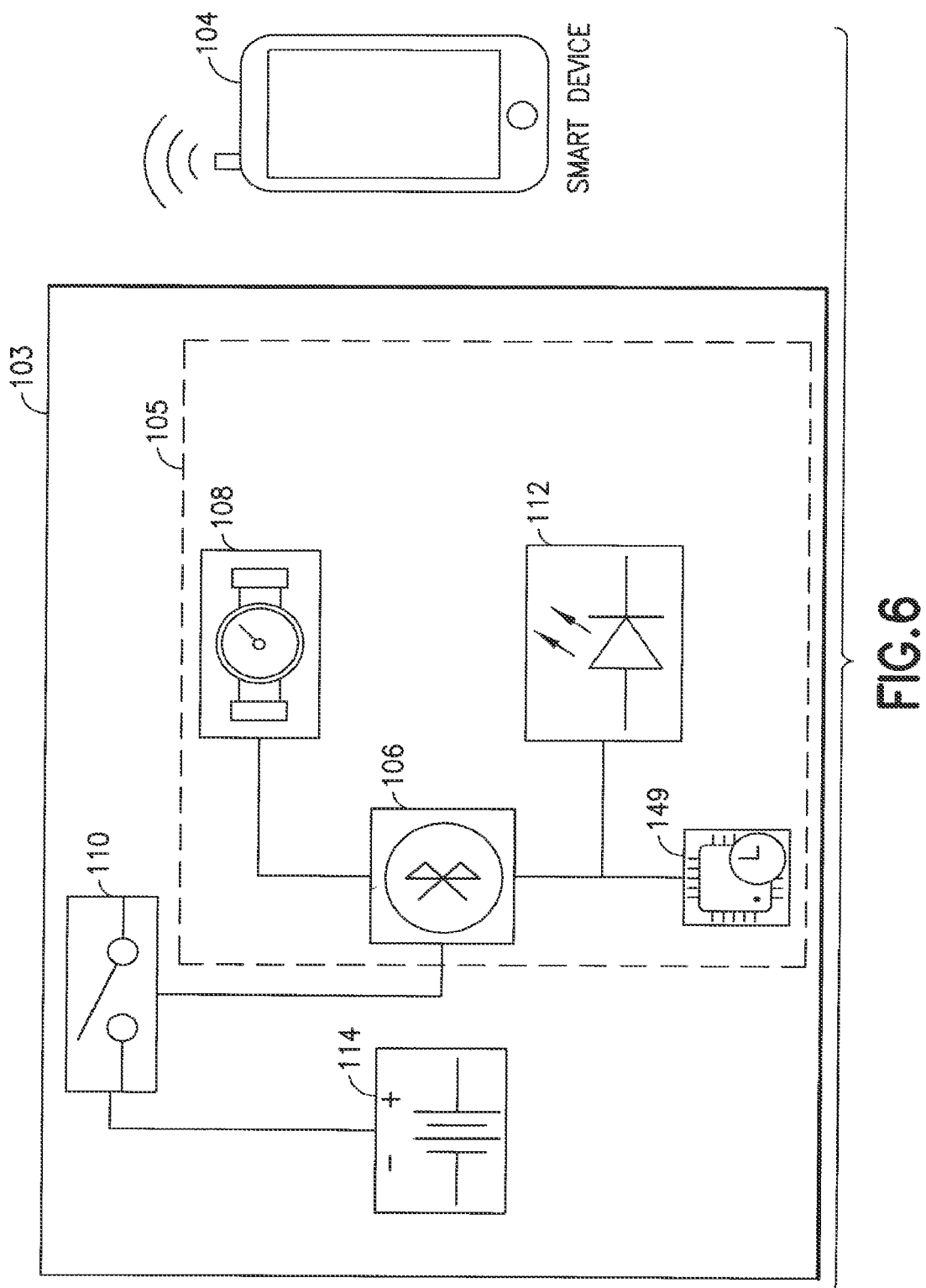
FIG. 6 is a block diagram of some of the components in the smart delivery system of FIG. 5 in accordance with an illustrative embodiment of the present invention.

In accordance with another illustrative embodiment of the present invention described with reference to FIGS. 5, 6 and 7, a memory-based smart delivery system 150 can be employed that comprises a delivery device 102 connected to another device 104 such as a smart phone via a wireless connection, and the delivery device 102 has a memory circuit (e.g., a Bluetooth™ chip 106 with memory or a separate memory device). Unlike the system 100 in FIG. 2, the embodiment illustrated in FIG. 5 is advantageous because dosing information is not lost when the smart device 104 is not paired with the delivery device 102. For example, as shown FIG. 6, the delivery device 102 or an add-on device (e.g., a pen needle adapter) for the delivery device can comprise a real-time clock 149 (e.g., Abracon AB-RTCMC real-time clock module or equivalent thereof). Sensed data from the sensor 108 and corresponding time stamps from the clock 149 can be stored in an on-board memory of the delivery device 102 or an adapter thereon (e.g., the Bluetooth™ chip 106 memory) and transmitted to the smart phone 104 at a later time than during real-time delivery and sensing operations. Thus, delivery data is not lost if the delivery device 102 and the smart phone 104 are not paired at the time of data capture by the sensor 108.

Figure 7:
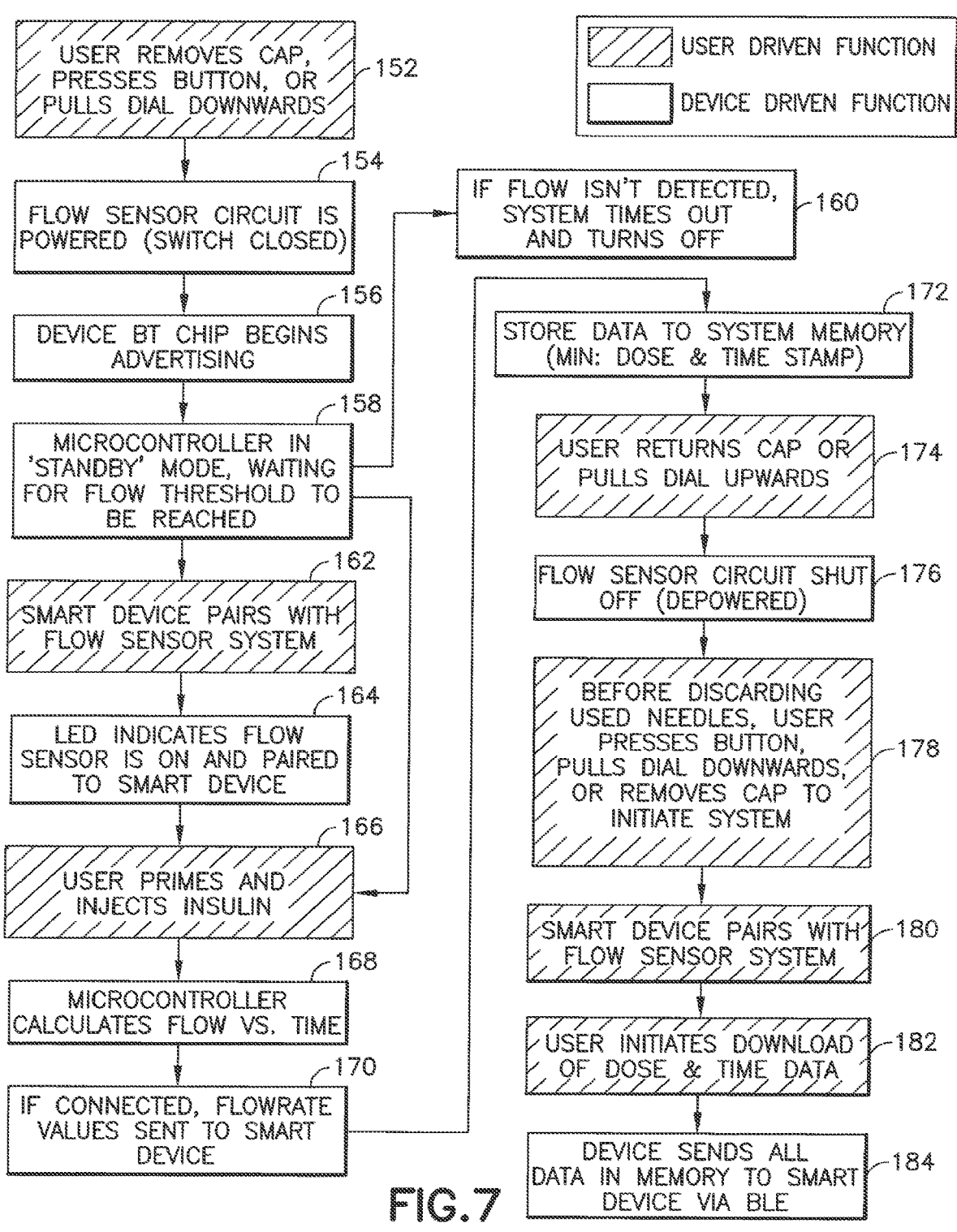
FIG. 7 is a flow chart depicting operations in the smart delivery system of FIG. 5 in accordance with an illustrative embodiment of the present invention.

With reference to FIG. 7, a user can remove a cap on the pen 102 and pull a dial thereon downwards or otherwise configure the pen for medication delivery (block 152). The delivery device 102 is configured such that user initiation of medication delivery (e.g., dialing a pen or pressing a button on a pump) causes the switch to close to allow supply of power to the flow sensing system (e.g., components indicated generally at 105 in FIG. 6) comprising the processor (e.g., in the Bluetooth™ chip 106), flow sensor 108, indicator(s) 112 and clock 149 (block 154). The Bluetooth™ chip 106 in the delivery device 102 is configured to commence advertising to pair with the smart phone 104 (block 156). The processing device (e.g., microcontroller in the Bluetooth™ chip or separate microcontroller in the delivery device 102) is configured to be in a "standby" mode until a designated flow threshold is reached (block 158). If flow is not detected within a designated period of time (e.g., 60 seconds), the flow sensing system 105 times out and is powered down by opening the switch 110 (block 160).

Once the smart device 104 pairs with the flow sensing system 105 in the delivery device 102 (block 162), the LED 112 is driven to indicate a first state, that is, the flow sensor 108 is powered on and the delivery device 102 is paired with the smart phone 104 (block 164), as shown in FIG. 7. The user can then prime the pen 102 or otherwise initiate injecting the medication via the delivery device 102 (block 166). The processing device 106 (e.g., microcontroller in the Bluetooth™ chip or separate microcontroller in the delivery device 102) is configured to determine with the aid of a clock 149 the flow of medication versus time during delivery (block 168). If paired or connected, the delivery device 102 provides flow rate values and other delivery data to the smart device 104 (block 170). The smart device 104 stores the received delivery data (e.g., sensed dose and time stamp, at a minimum) to system memory (block 172). The user returns the cap to the pen or pulls the pen dose dial upwards or otherwise operates the pen to return to a non-dosing operational state (block 174), and the flow sensing system 105 is then powered off (block 176).

Another advantage of a memory-based smart delivery system 150 is that the processing device 106 in the delivery device 102 can be configured to transmit all data in the device 102 memory before the device 102 or an adapter thereof containing the flow sensing system 105 is discarded so as not to lose any delivery infomatics that have not been provided to a connected smart device 104. With continued reference to FIG. 7, before discarding the device 102 or a replaceable part thereof (e.g., pen needle adapter), the user presses a button, pulls a dose dial downward, removes pen cap, or otherwise initiates the flow sensing system 105 (block 178). The processing device 106, in turn, is configured to commence pairing the flow sensing system 105 with the smart device 104 or otherwise connecting to the smart device 104 (block 180). The user initiates or the processing device 106 automatically initiates the downloading of stored delivery data (e.g., at least dose and time data) (block 182) into an on-board memory or otherwise accessing the stored delivery data or at least a part of the stored data (e.g., the values generated since the last system pairing or transmission to the smart device 104). The delivery device 102 or at least its flow sensing system 105 sends the stored delivery data to the smart device 104 (e.g., via Bluetooth™) (block 184).

In accordance with another illustrative embodiment of the present invention described with reference to FIGS. 8, 9 and 10, a near-field communication or NFC-enabled smart delivery system 190 can be employed that comprises a delivery device 102 with a NFC chip (e.g., an RFID chip) connected to another device 104 such as a NFC-enabled smart phone via a NFC wireless connection. Unlike the systems 100 in FIGS. 2 and 150 in FIG. 5, the embodiment illustrated in FIG. 8 requires that the delivery device 102 and smart phone 104 be in relatively close proximity (e.g., on the order of 10 centimeters).

Figure 9:
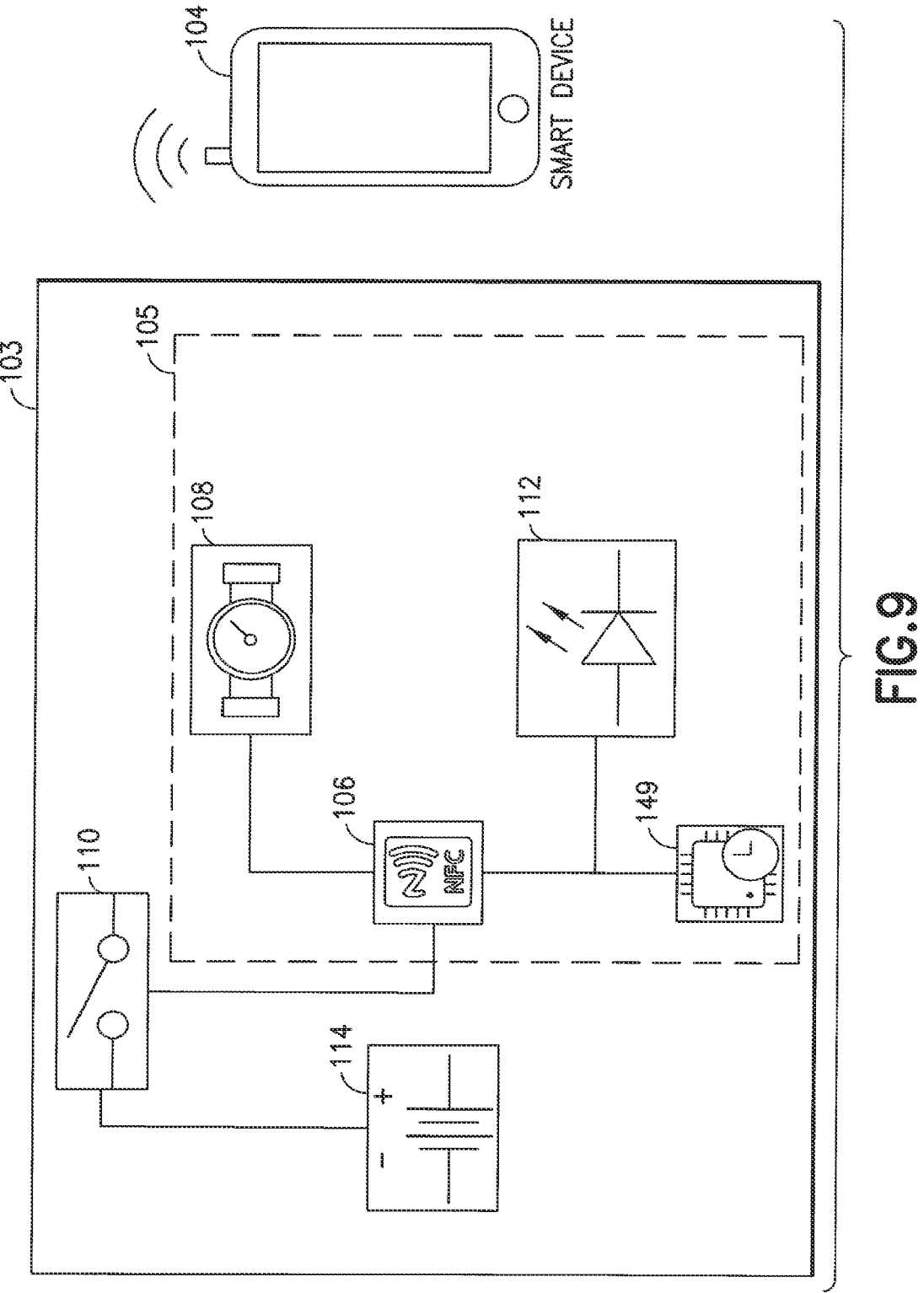
FIG. 9 is a block diagram of some of the components in the smart delivery system of FIG. 8 in accordance with an illustrative embodiment of the present invention.

With reference to FIG. 9, the processing device 106 can be a NFC chip 106 with memory such as, for example, a TI RF430FRL152H, which has a microprocessor, memory and flow sensor interface. Using a NFC-enabled smart phone 104, the dose history of the delivery device 102 stored in its memory circuit can be downloaded when the delivery device 102 is scanned by the NFC-enabled smart phone 104. The NFC-enabled smart delivery system 190 is therefore advantageous because delivery data is saved regardless of the proximity of the smart device 104 to the delivery device 102. Also, pairing can be automated. In addition, the NFC chip may be smaller in form factor than, for example, a Bluetooth™ chip allowing for more compact electronics 103 in a delivery device 102, which can be advantageous for implementing various delivery device 102 form factors.

Figure 10:
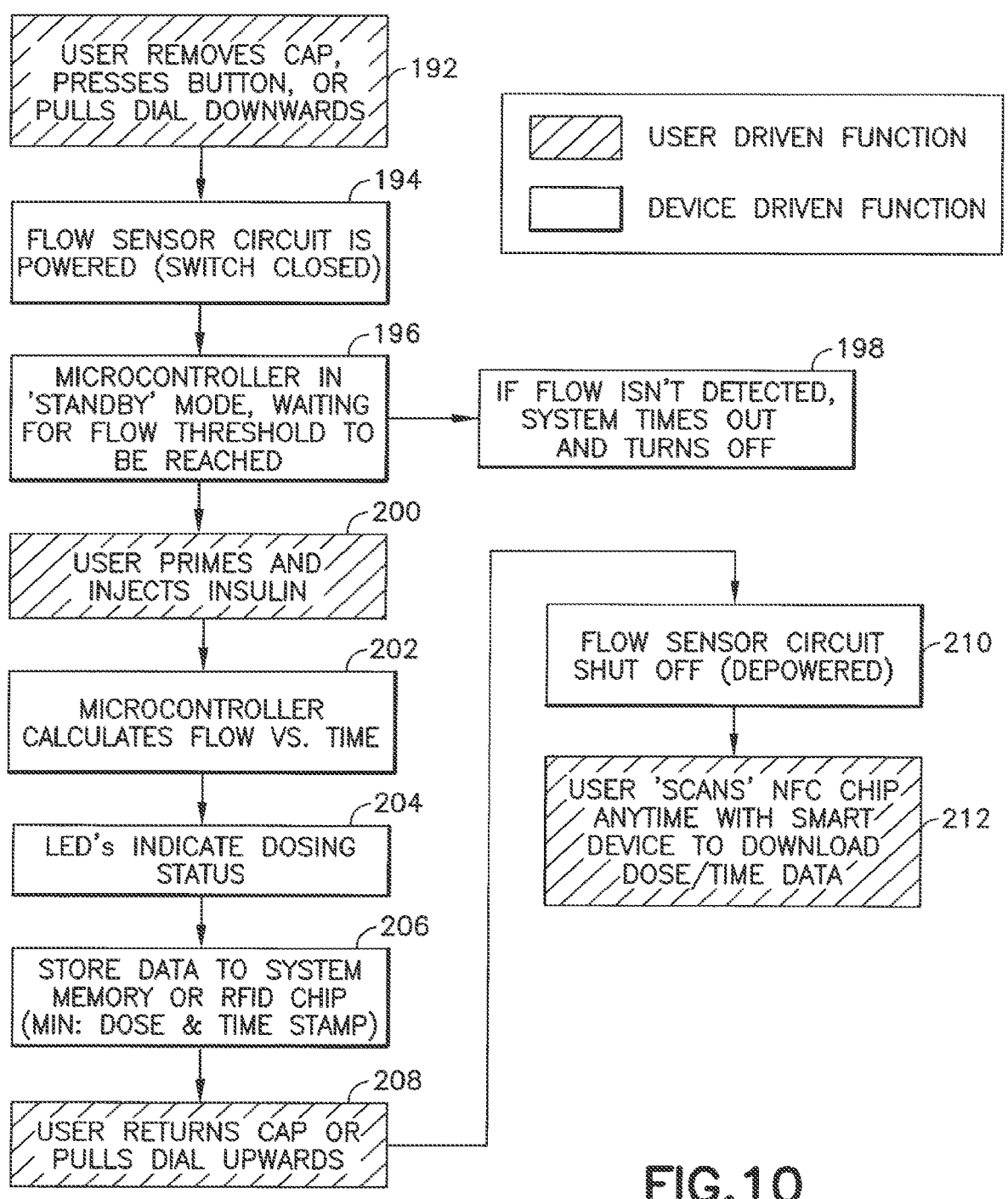
FIG. 10 is a flow chart depicting operations in the smart delivery system of FIG. 8 in accordance with an illustrative embodiment of the present invention.

With reference to FIG. 10, a user can remove a cap on the pen 102 and pull a dial thereon downwards or otherwise configure the pen for medication delivery (block 192). The delivery device 102 is configured such that user initiation of medication delivery (e.g., dialing a pen or pressing a button on a pump) causes the switch to close to allow supply of power to the flow sensing system (e.g., components indicated generally at 105 in FIG. 6) comprising the processor (e.g., in the NFC chip 106), flow sensor 108, indicator(s) 112 and clock 149 (block 194). The processing device 106 (e.g., microprocessor in the NFC chip or separate microcontroller in the delivery device 102) is configured to be in a "standby" mode until a designated flow threshold is reached (block 196). If flow is not detected within a designated period of time, the flow sensing system 105 times out and is powered down by opening the switch 110 (block 198).

The user can then prime the pen 102 or otherwise initiate injecting the medication via the delivery device 102 (block 200). The processing device 106 (e.g., microprocessor in the NFC chip or separate microcontroller in the delivery device 102) is configured to determine with the aid of a clock 149 the flow of medication versus time during delivery (block 202). An LED 112 on the delivery device 102 is driven to indicate that dosing is in progress (block 204). The delivery device 102 stores delivery data to its memory (e.g., sensed dose and time stamp, at a minimum), as indicated in block 206. The user returns the cap to the pen or pulls the pen dose dial upwards or otherwise operates the pen to return to a non-dosing operational state (block 208), and the flow sensing system 105 is then powered off (block 210). The user can, at any time, use the NFC-enabled smart device 104 to scan the delivery device 102 to retrieve the delivery data (e.g., dose and corresponding time stamp data, at a minimum, and optionally other data such as determined flow rates at different times) stored in the RFID chip 106, as indicated in block 212.

In accordance with another illustrative embodiment of the present invention described with reference to FIGS. 11, 12 and 13, a hybrid NFC-enabled and Bluetooth™-enabled smart delivery system 220 can be employed that comprises a delivery device 102 with a NFC chip and a Bluetooth™ chip connected to another device 104 such as a NFC-enabled and Bluetooth™-enabled smart phone with via a NFC and/or Bluetooth™ wireless connection. Unlike the systems 100 in FIGS. 2 and 150 in FIGS. 5 and 190 in FIG. 8, the embodiment illustrated in FIG. 11 allows for delivery data history to be downloaded or otherwise retrieved from the delivery device 102 at any time, and data synchronization can occur between the delivery device 102 and the smart device 104 at any time when they are connected. The devices 102 and 104 can pair when the delivery device 102 is in proximity to the smart device 104.

Figure 12:
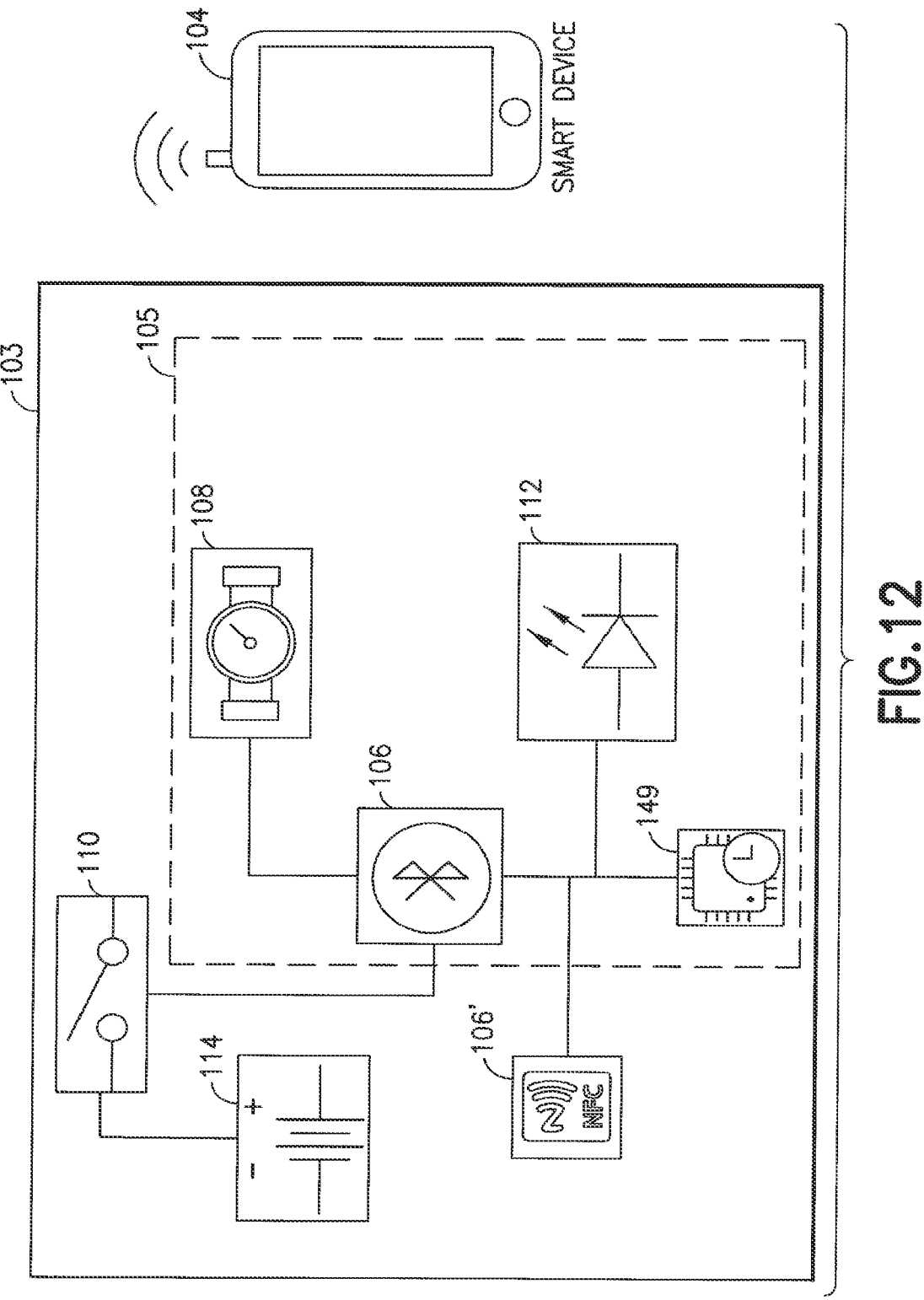
FIG. 12 is a block diagram of some of the components in the smart delivery system of FIG. 11 in accordance with an illustrative embodiment of the present invention.

With reference to FIG. 12, the processing device can be a Bluetooth™ chip 106 and a NFC chip 106'. The Bluetooth™ chip 106 can be, for example, a Bluetooth™ low energy LE chip such as TI CC 2541 which has an on-board processor and memory for synchronization and other Bluetooth™ operations. The NFC chip 106' can be a simple NFC chip (e.g., a RFID chip that can be scanned but does not necessarily have a processor).

Figure 13:
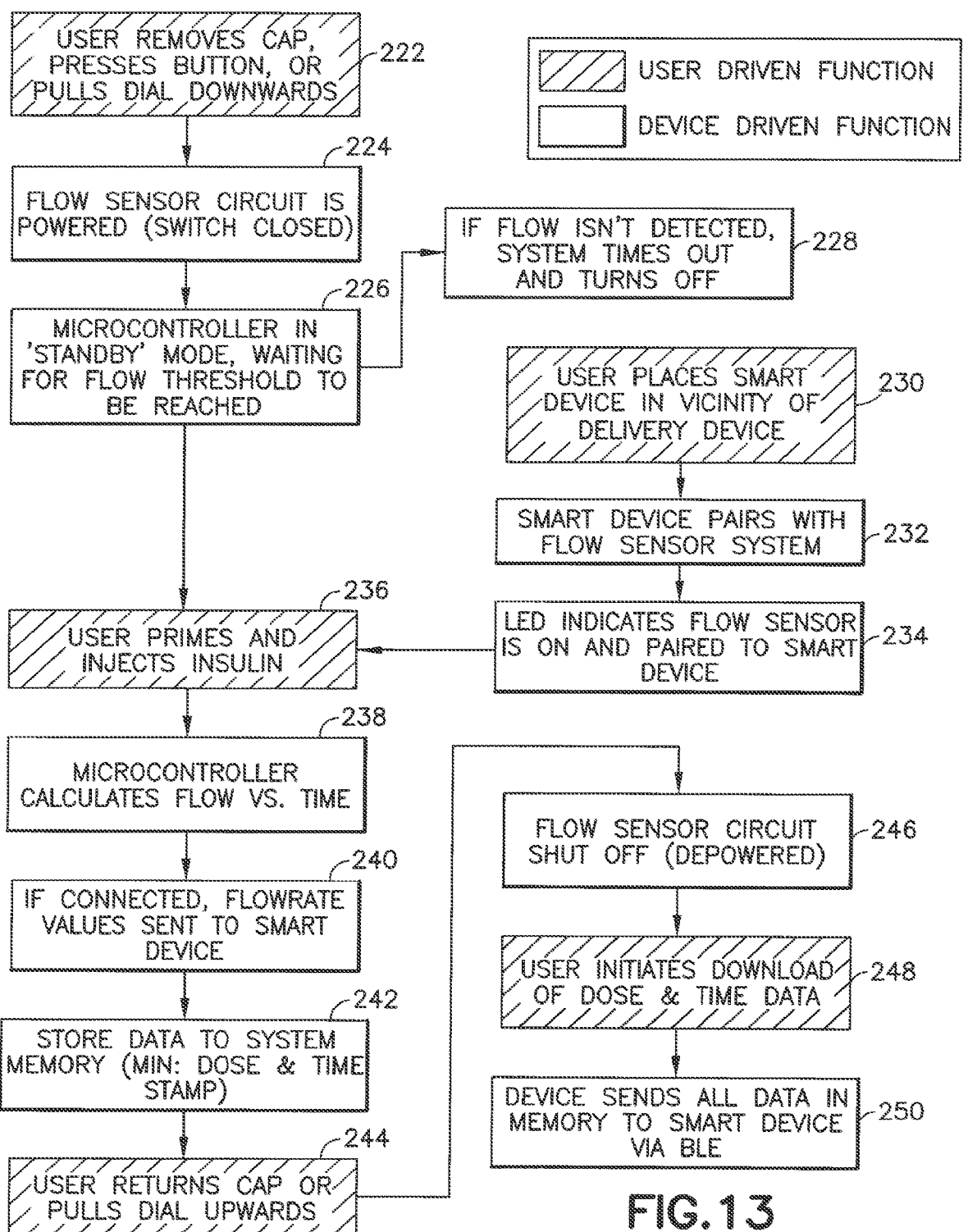
FIG. 13 is a flow chart depicting operations in the smart delivery system of FIG. 11 in accordance with an illustrative embodiment of the present invention.

With reference to FIG. 13, a user can remove a cap on the pen 102 and pull a dial thereon downwards or otherwise configure the pen for medication delivery (block 222). The delivery device 102 is configured such that user initiation of medication delivery (e.g., dialing a pen or pressing a button on a pump) causes the switch to close to allow supply of power to the flow sensing system (e.g., components indicated generally at 105 in FIG. 12) comprising the processor (e.g., in the Bluetooth™ chip 106), flow sensor 108, indicator(s) 112 and clock 149 (block 224). The processing device (e.g., microcontroller in the Bluetooth™ chip or separate microcontroller in the delivery device 102) is configured to be in a "standby" mode until a designated flow threshold is reached (block 226). If flow is not detected within a designated period of time, the flow sensing system 105 times out and is powered down by opening the switch 110 (block 228).

With reference to block 230, a user can place the smart device 104 in the vicinity of the delivery device 102, that is, on the order of 10 centimeters for NFC connectivity or on the order of 10 meters for Bluetooth™ connectivity. Once the smart device 104 pairs with the flow sensing system 105 in the delivery device 102 (block 232), the LED 112 is driven to indicate that the flow sensor 108 is powered on and the delivery device 102 is paired with the smart phone 104 (block 234. The user can then prime the pen 102 or otherwise initiate injecting the medication via the delivery device 102 (block 236). The processing device 106 (e.g., microcontroller in the Bluetooth™ chip or separate microcontroller in the delivery device 102) is configured to determine with the aid of a clock 149 the flow of medication versus time during delivery (block 238). If paired or connected, the delivery device 102 provides flow rate values and other delivery data to the smart device 104 (block 240). The smart device 104 stores the received delivery data (e.g., sensed dose and time stamp, at a minimum) to system memory (block 242). The user returns the cap to the pen or pulls the pen dose dial upwards or otherwise operates the pen to return to a non-dosing operational state (block 244), and the flow sensing system 105 is then powered off (block 246).

Another advantage of a memory-based smart delivery system 150 is that the processing device 106 can be configured to transmit all data in the device 102 memory to the smart device 104 at any time, such as before the delivery device 102 or an adapter thereof containing the flow sensing system 105 is discarded so as not to lose any delivery infomatics that have not been provided to a connected smart device 104. With continued reference to FIG. 12, before discarding the device 102 or a replaceable part thereof (e.g., pen needle adapter) for example, the user presses a button, pulls a dose dial downward, removes pen cap, or otherwise initiates download of delivery data (e.g., at least dose and time data) (block 248). Either the user initiates or the processing device 106 automatically initiates the downloading of stored delivery data. The stored delivery data (e.g., at least dose and time data) or at least a part of the stored delivery data (e.g., the values generated since the last system pairing or transmission to the smart device 104) in the delivery device 102 can be downloaded or accessed for storage to a memory device associated with the smart device 104. For example, the delivery device 102 or at least its flow sensing system 105 can send the stored delivery data to the smart device 104 via Bluetooth™ (block 250).

Figure 8:
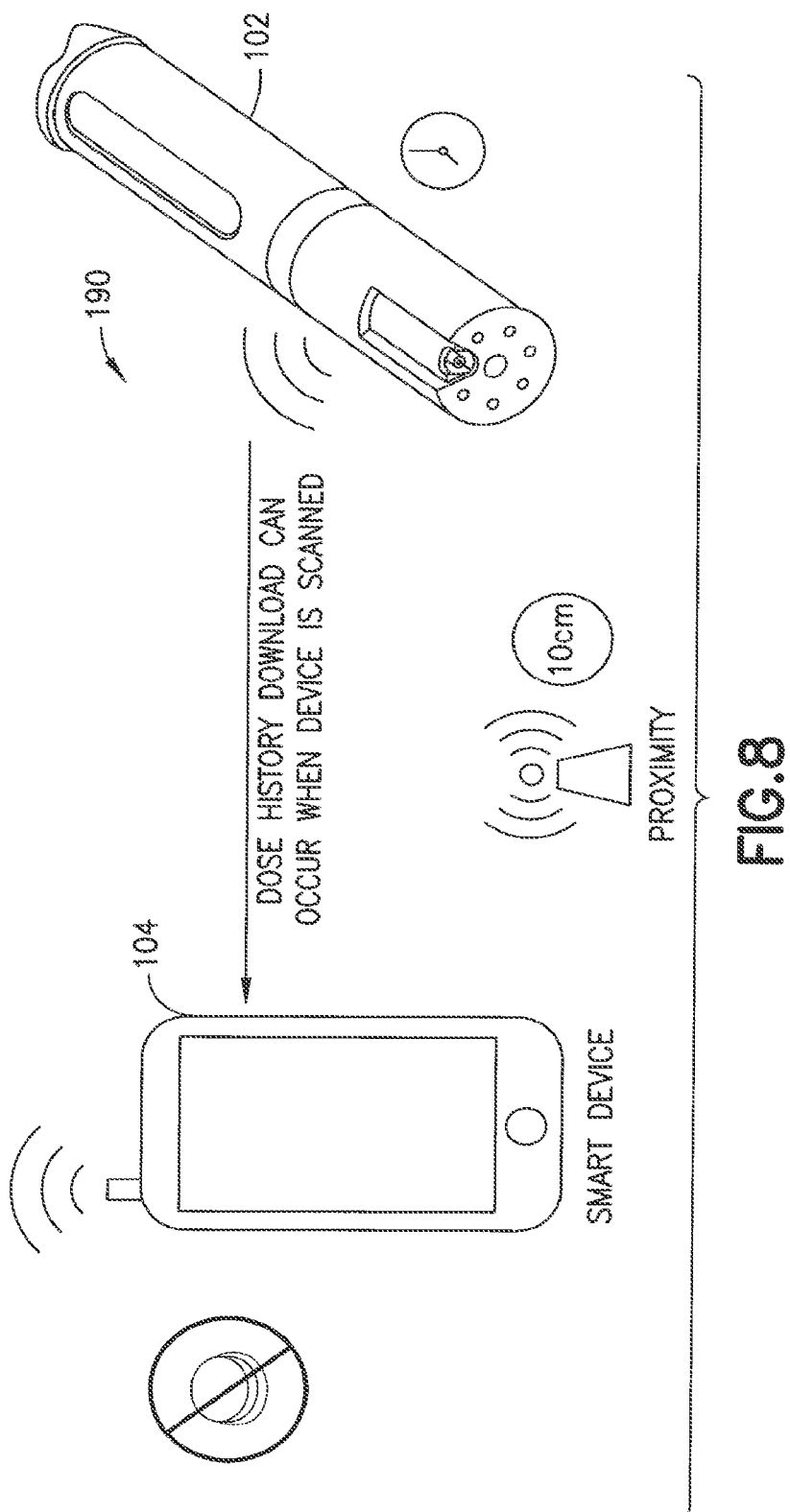
FIG. 8 depicts a near-field communication or NFC-enabled smart delivery system in accordance with an illustrative embodiment of the present invention.
Figure 11:
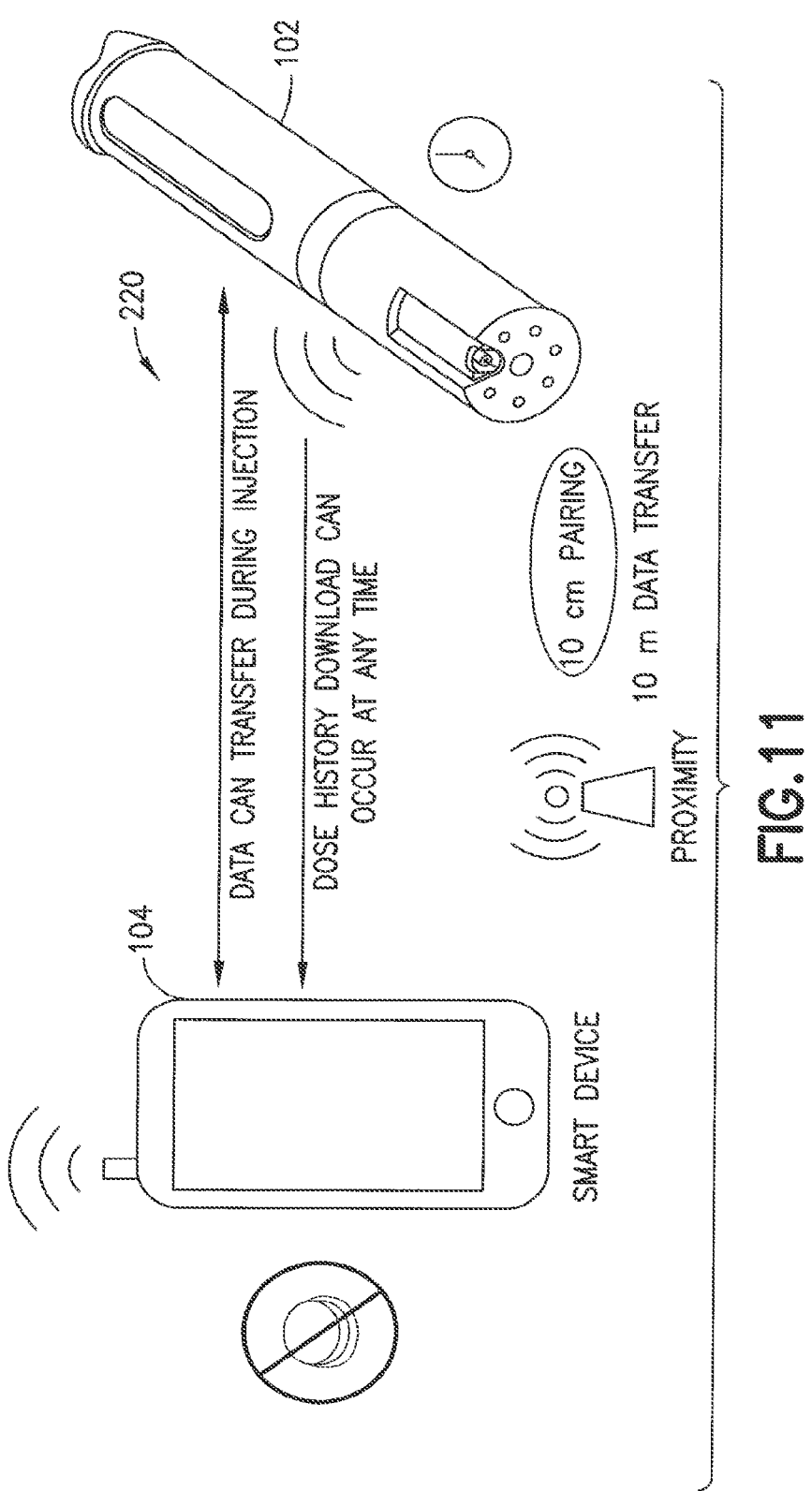
FIG. 11 depicts a hybrid NFC-enabled and Bluetooth™-enabled smart delivery system in accordance with an illustrative embodiment of the present invention.

Unlike the systems 100 in FIGS. 2 and 150 in FIGS. 5 and 190 in FIG. 8, the embodiment illustrated in FIG. 11 having Bluetooth™ and NFC connectivity and on-board storage of dose history realizes a number of advantages such as allowing for delivery data to be saved regardless of the proximity of the delivery device 102 to the smart phone 104. Also, pairing can be automated. In addition, delivery data transfer can occur even after the batteries 114 are depleted. More specifically, the NFC chip's on-board processor has integrated memory, and dose history data or other delivery-related can be stored at this location. This stored data can be transferred to a smart device 104 regardless of the delivery device battery state because the NFC chip can be powered by a 'scan' (e.g., an NFC-enabled smart phone 104 scanning the delivery device 102 such that the data in the NFC chip can be downloaded to the phone 104). The Bluetooth™ chip 106, by contrast, can store and transmit dose data, but it cannot be powered by the smart device 104 in the same manner as the NFC chip 106' when scanned. When the on-board batteries of a Bluetooth™-only device have been depleted, the data is lost. Having a Bluetooth™ chip 106 on-board the delivery device 102 with an NFC chip 106' as shown in FIG. 12 enables 'live' capture of flow-related data through the cannula but is further advantageous since NFC chips can only be scanned in discrete ways. The Bluetooth™ connectivity, however, allows for more convenient and automated monitoring of dosing as the user is delivering medication. Finally, the NFC chip 106' can enable quick and automated pairing of the Bluetooth™ system (e.g., the Bluetooth™ chip 106 with the connected device 104). For example, tapping the smart device 104 to the NFC chip 106' in the delivery device 102 can activate the pairing process and obviate the need for the user to manually pair the delivery 102 vice to the phone or connected device 104.

In accordance with another illustrative embodiment of the present invention described with reference to FIGS. 14, 15 and 16, a wireline connected smart delivery system 260 can be employed that comprises a delivery device 102 with a cable or other wire and associated cable interface or connector 262 (e.g., a mini USB cable and connector) for hardwire connection to a smart device 104 to transfer delivery data. Unlike the systems 100 in FIGS. 2 and 150 in FIGS. 5 and 190 in FIGS. 8 and 220 in FIG. 11, the embodiment illustrated in FIGS. 14 and 15 allows for the use of a processing circuit 106 such as a microprocessor (e.g., a Kinetis KL02 with memory) which may be smaller in form factor than, for example, a Bluetooth™ chip, allowing for more compact electronics 103 in a delivery device 102, which can be advantageous for implementing various delivery device 102 form factors. The smart delivery system 260 allows for synchronization of delivery data from the delivery device 102 to the smart device 104 any time the devices 102 and 104 are connected by the cable.

Figure 16:
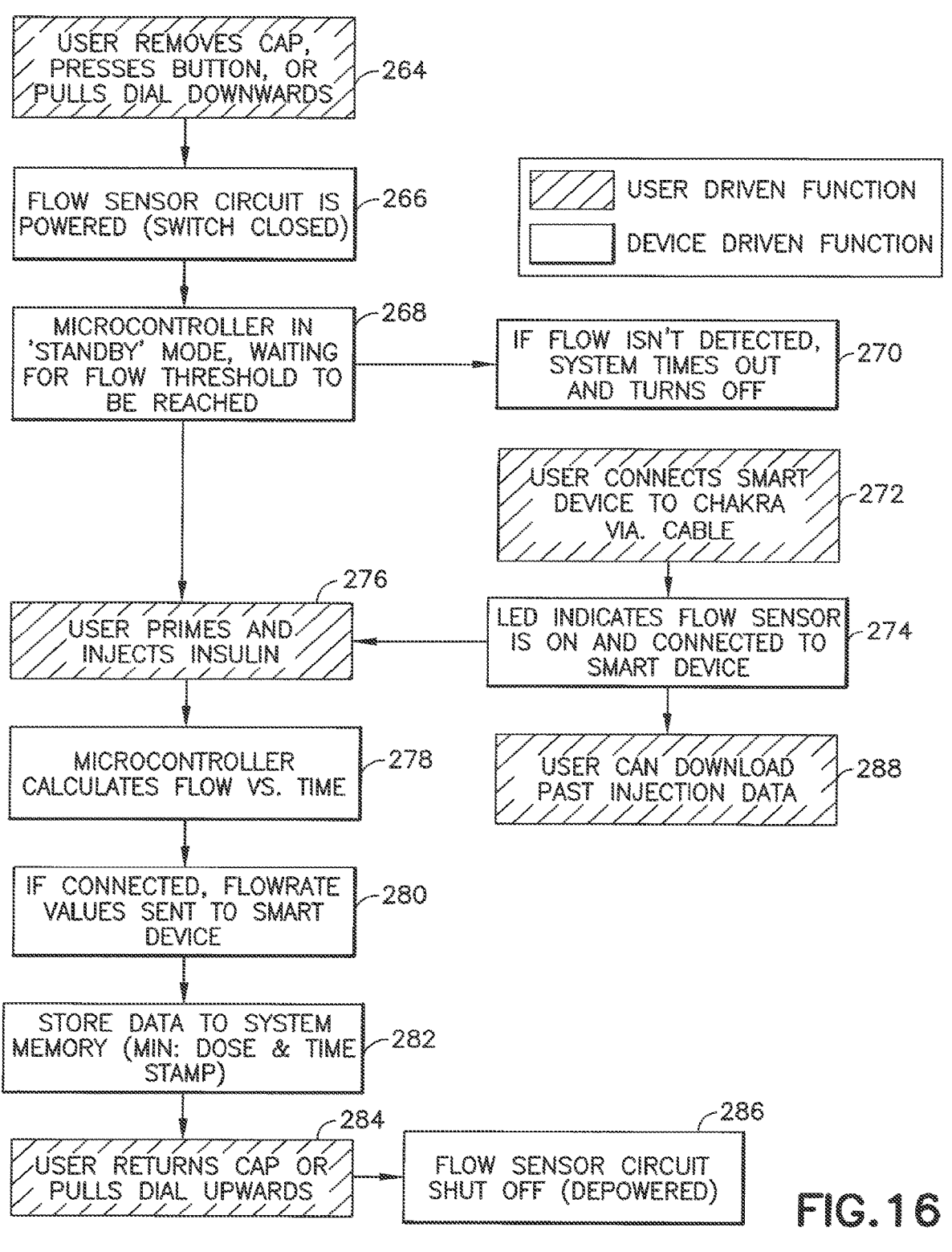
FIG. 16 is a flow chart depicting operations in the smart delivery system of FIG. 14 in accordance with an illustrative embodiment of the present invention.

With reference to FIG. 16, a user can remove a cap on the pen 102 and pull a dial thereon downwards or otherwise configure the pen for medication delivery (block 264). The delivery device 102 is configured such that user initiation of medication delivery (e.g., dialing a pen or pressing a button on a pump) causes the switch to close to allow supply of power to the flow sensing system (e.g., components indicated generally at 105 in FIG. 12) comprising the microprocessor 106, flow sensor 108, indicator(s) 112 and clock 149 (block 266). The microprocessor 106 is configured to be in a "standby" mode until a designated flow threshold is reached (block 268). If flow is not detected within a designated period of time, the flow sensing system 105 times out and is powered down by opening the switch 110 (block 270).

With reference to block 272, a user connects the delivery device 102 to the smart device 104. The LED 112 is driven to indicate that the flow sensor 108 is powered on and the delivery device 102 is connected to with the smart phone 104 (block 274). Once a user sees via the LED that the devices 102 and 104 are connected and flow sensing is on, the user can then prime the pen 102 or otherwise initiate injecting the medication via the delivery device 102 (block 276). The microprocessor 106 is configured to determine with the aid of a clock 149 the flow of medication versus time during delivery (block 278). If connected, the delivery device 102 provides flow rate values and other delivery data to the smart device 104 (block 280). The smart device 104 stores the received delivery data (e.g., sensed dose and time stamp, at a minimum) to system memory (block 282). The user returns the cap to the pen or pulls the pen dose dial upwards or otherwise operates the pen to return to a non-dosing operational state (block 284), and the flow sensing system 105 is then powered off (block 286).

Another advantage of a memory-based smart delivery system 260 is that the processing device 106 can be configured to transmit all data in the device 102 memory to the smart device 104 at any time, such as before the delivery device 102 or an adapter thereof containing the flow sensing system 105 is discarded so as not to lose any delivery infomatics that have not been provided to a connected smart device 104. With continued reference to FIG. 16, before discarding the device 102 or a replaceable part thereof (e.g., pen needle adapter) for example, the user can download past delivery data (e.g., doses and times of past injections at a minimum and optionally determined flow data) if a cable is connected between the devices 102 and 104, and the user presses a button, pulls a dose dial downward, removes pen cap, or otherwise initiates download of delivery data (e.g., at least dose and time data) (block 288). Either the user initiates or the processing device 106 automatically initiates the downloading of stored delivery data. The stored delivery data (e.g., at least dose and time data) or at least a part of the stored delivery data (e.g., the values generated since the last system download can be provided from the delivery device 102 to the smart device 104.

Figure 14:
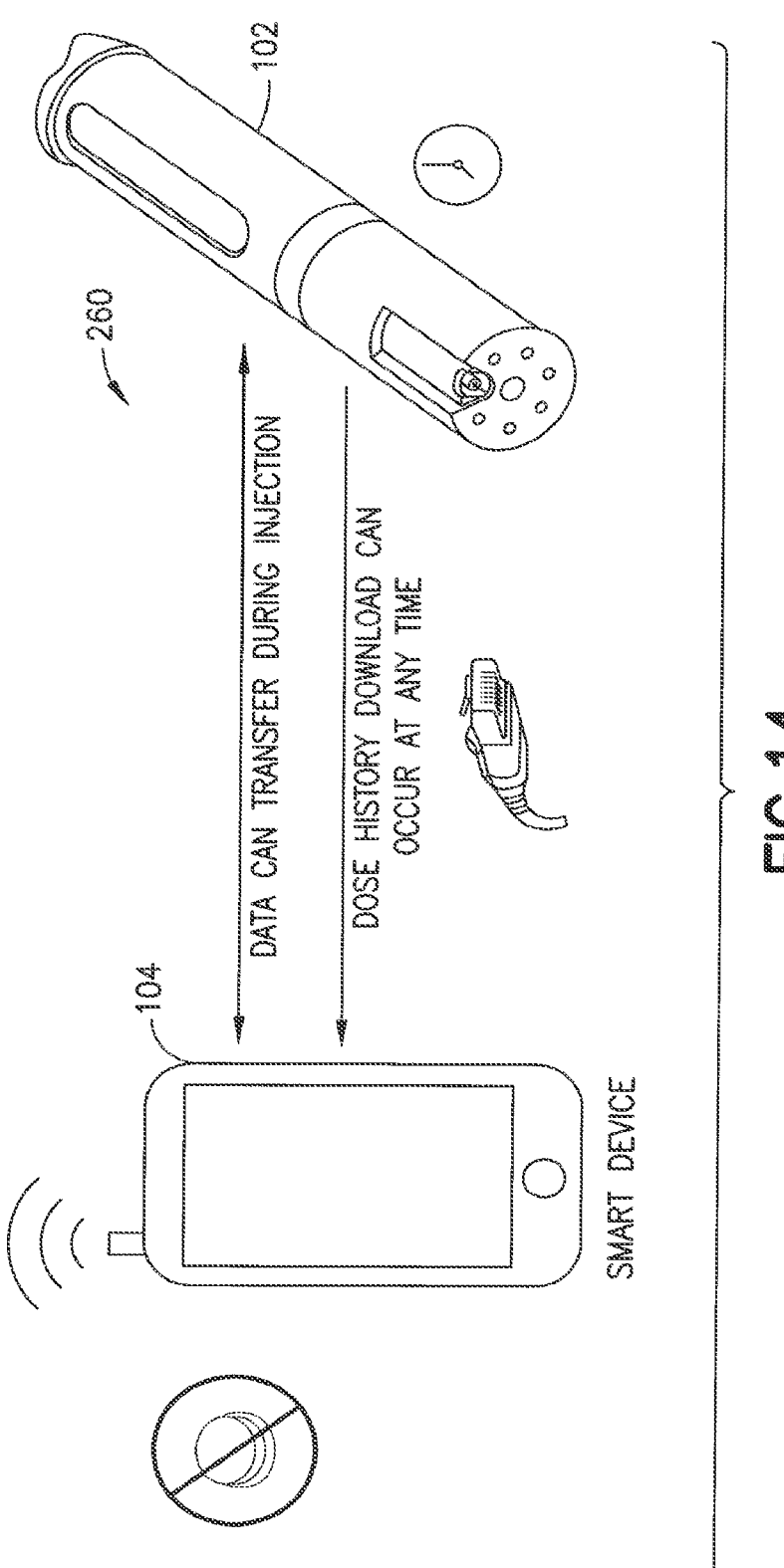
FIG. 14 depicts a wireline connected smart delivery system in accordance with an illustrative embodiment of the present invention.
Figure 15:
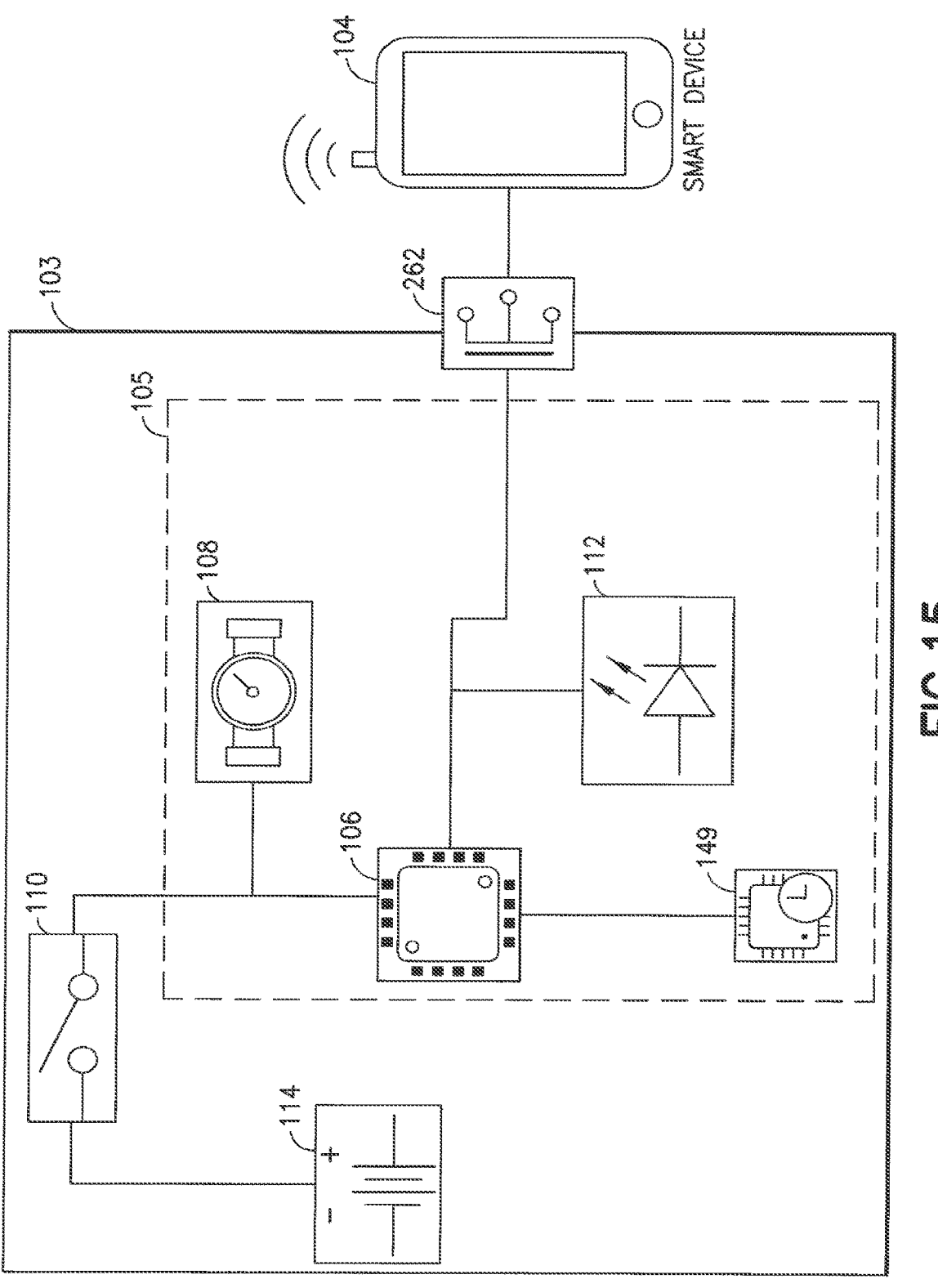
FIG. 15 is a block diagram of some of the components in the smart delivery system of FIG. 14 in accordance with an illustrative embodiment of the present invention.

It is to be understood that a smart delivery system can have different combinations of the components and operations described above in the illustrative systems 100 (FIGS. 2, 3 and 4), 150 (FIGS. 5, 6 and 7), 190 (FIGS. 8, 9 and 10), 220 (FIGS. 11, 12 and 13), and 260 (FIGS. 14, 15 and 16). Whatever the configuration, the smart delivery system comprises a delivery device 102 and a connected or paired smart device 104 wherein flow data in obtained from a flow sensor in the delivery device 102, and processing device(s) in one or both of the devices 102 and 104 can get flow data from the sensor during dosing (e.g., dose, time, how much time to deliver dose, and/or flow rate). For example, during delivery, flow rate data indicates issues such as clogging and alert to user can be generated during dosing. For example, the delivery device 102 can be configured to capture time of dose and send with flow data and total amount delivered data to a smart phone 104.

Wireless communications between the devices 102 and 104 have been illustrated as BLE or NFC. It is to be understood, however, that different wireless communication technologies can be used such as WiFi/wireless local area network (WLAN)/IEEE 802.11 standard channel frequencies (e.g., Wi-Fi 802.11 for the 2.4 GHz ISM band, or 3.6 GHz or 5 GHz WiFi bands, or White-Fi band of 479-710 MHz), and ZigBee or other IEEE 802.15.4-based personal area network protocol, among other wireless communication formats or protocols and associated operating frequencies, by way of non-limiting examples.

As illustrated in connection with FIGS. 4, 7, 10, 13 and 16, the devices 102 and 104 can communicate in real-time, or communication can be deferred, depending on pairing of the delivery device 102 with an external device 104 such as smart phone or iPad or lap top or other computing device. The delivery device 102 is unique in terms of the time of data transfer, that is, when flow data is sent to the smart phone 104. For example, the delivery data or dose capture data can be sent during dosing, when dosing is complete, and later when pairing or a USB connection occurs. One or more LEDs 112 on the delivery device 102 and/or indicators on the smart device 104 can let a user know a number of important states of the delivery device 102 such as when its flow sensing system 105 is powered on and the device is ready for dosing and delivery data capture, when the device 102 is paired for real-time transfer of delivery data to the smart device 104, when dosing is complete and a user can remove the delivery device needle (e.g., flow rate indicates injection is complete, or a processor determines the flow over a designated period of time matches an inputted dose amount), among other states.

The smart phone 104 can have one or more delivery data and medicine or medical condition management apps. For example, for diabetes management, the smart phone 104 can have an app to collect glucose readings, information related to carbohydrate intake, and information related exercise to assist the user with better diabetes management decisions. Diabetes management apps to date have been missing important additional information regarding dosing, that is, accurate and reliable dose capture or delivery data.

In accordance with an embodiment of the present invention, the smart device 104 can be provided with an app or otherwise programmed or configured to receive dose capture data from a connected or paired delivery device 102 and, for example, to confirm a designated dose was effectively delivered based on detected flow data received from the delivery device. For example, a prescribed diabetes management regimen of 20 units of insulin 3 times per day can be programmed into the app of a smart device. If the user dials the dose incorrectly into a connected or paired medication pen 102 relative to prescribed regimen (e.g., 10 units instead of 20 units), the app on phone can generate an alarm to alert user when the capture dose data indicates that the detected actual delivered amount is different from the prescribed amount. This significantly reduces user mishandling of a delivery device 102 and provides timely detection of a malfunctioning delivery device 102. This represents a significant advantage over conventional delivery devices, where a user does not hold the pen needle long enough to complete delivery, or misuses the device and causes it to leak, for example. Further, if a dose is skipped altogether, the app can alarm the user or caregiver (e.g., parent) by having the smart device send a text to the caregiver's mobile phone. In addition, the smart phone 104 delivery data app aggregates important delivery data and can share it with healthcare providers, insurance providers, and so on.

With continued reference to the illustrative systems described above (e.g., smart delivery systems 100 (FIGS. 2, 3 and 4), 150 (FIGS. 5, 6 and 7), 190 (FIGS. 8, 9 and 10), 220 (FIGS. 11, 12 and 13), and 260 (FIGS. 14, 15 and 16)), transfer of data between devices during data capture requires the smart device 104 to be paired or connected to a delivery device 102 that is configured to sense a characteristic of data delivery. A number of examples described above use BLE pairing between the devices 102 and 104. An advantage of BLE or other protocol that enables automated pairing (e.g., based on proximity of the devices or signal strength) is that a user knows that he or she can get dose capture data as long as the devices 102 and 104 are connected. Alternatively, if the delivery device 102 is configured to store dose capture data or delivery data, a user knows that pairing between devices 102 and 104 is not required to capture delivery data at the time of injection and that stored dose capture data can be retrieved or otherwise accessed at a later time. For example, the user can connect devices 102 and 104 via a mini USB cable or, if the devices 102 and 104 are NFC-enabled, the user need only bring a NFC-enabled phone 104 proximal to the smart pen, or smart pen needle or other smart delivery device 102 to automatically transmit delivery data to the device 104, even if the battery in the delivery device 102 is dead. Further, the delivery device 102 can have more than one wireless antenna (e.g., have NFC and BLE antennae) for more flexibility in terms of when and under what conditions the delivery device 102 synchronizes with the smart device 104.

In accordance with different embodiments of the present invention, the electronics 105 can be deployed using different form factors depending on the form factor of the delivery device or adapter/attachment thereof 102 that cooperates with a connected device 104. For example, the electronics 105 can be deployed within an electronic exchange system attached to a needle assembly of a medication pen. In an alternative embodiment, the flow sensor 108 can be deployed along a fluid path in a wearable pump or in patch pump.

As stated above, one or more sensors 108 can be used in a delivery device or attachment or adapter 102 that cooperates with another device 104. Different types of sensors 108 can be used such as, but not limited to, Micro-Electro-Mechanical Systems (MEMS) flow sensors to provide an informatically-enabled drug delivery device 102 such as a patch pump. Flow sensing, particularly MEMS flow sensors, can include coriolis, capacitance, and thermal sensors such as Time of Flight (ToF) sensors used to determine the volume of drug delivered by a drug delivery device such as a patch pump, as well as sensing conditions such as occlusion or low volume. An example of a MEMS-type pressure sensor 30 is a pressure sensor available from Amphenol Advanced Sensors or MEMS Pressure Sensors Puerto Rico LLC. MEMS sensors typically come prepackaged by a manufacturer. MEMS sensors contain not only the specific MEMS sensing component, which is necessarily very small, but also related electronics and circuitry.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed. Accordingly, additional embodiments are possible and are intended to be encompassed within this specification and the scope of the invention. The specification describes specific examples to accomplish a more general goal that may be accomplished in another way.

The invention claimed is:

1. A medication delivery device, comprising:
a sensor configured to sense flow of medication from the medication delivery device
(MDD) to a patient at a delivery site;
a processing device configured to receive sensor data from the sensor; and
an indicator;
wherein the processing device is configured to:
operate the indicator to indicate that the MDD may be removed from the delivery site when a predetermined amount of time has elapsed after the sensor data that the processing device receives corresponds to a sensed flow rate of medication from the MDD being zero.

2. The medication delivery device of claim 1, further comprising a cannula, wherein:
the sensor is configured to sense flow of medication from the medication delivery device (MDD) through the cannula to the patient at the delivery site; and
the processing device is configured to operate the indicator to indicate that the cannula may be removed from the delivery site when the predetermined amount of time has elapsed after the sensor data that the processing device receives corresponds to the sensed flow rate of medication from the MDD being zero.

3. The medication delivery device of claim 1, wherein the medication delivery device comprises at least one of a medicine injection pen, a pen needle, a pen needle attachment, a medicine delivery pump, a wearable pump, or a patch pump.

4. The medication delivery device of claim 1, wherein the sensor is at least one of a flow sensor, a thermal flow sensor, a pressure sensor, or a micro-electro-mechanical system (MEMS) sensor.

5. The medication delivery device of claim 1, wherein the sensor data comprises voltage values corresponding to the sensed flow rate of medication from the MDD.

6. The medication delivery device of claim 1, wherein the indicator comprises a light emitting diode (LED).

7. The medication delivery device of claim 1, wherein:
the MDD further comprises a time clock and a memory device; and
the processing device is configured to store sensor data and corresponding time stamps obtained via the time clock.

8. The medication delivery device of claim 1, wherein the processing device is configured to:
analyze the sensed flow rate of medication from the MDD;
determine if a clog is present in the MDD based on the sensed flow rate of medication from the MDD; and
upon determination that the clog is present in the MDD, operate the indicator to indicate the clog is present in the MDD.

9. The medication delivery device of claim 1, further comprising a wireless communication circuit configured to transmit the sensor data from the MDD to an external device on a wireless link.

10. The medication delivery device of claim 9, wherein:
the processing device is configured to transmit flow data to the external device;
the external device is configured to determine whether a delivered dose differs from a prescribed dose based on the flow data; and
the external device is configured to generate an alarm if the delivered dose differs from a prescribed dose.

11. The medication delivery device of claim 9, wherein the external device is configured to:
provide time stamps to the sensor data based on when the sensor data is received and store the sensor data and corresponding time stamps; and
determine the sensed flow rate of the delivery of the medication to the patient over time using the sensor data and the time stamps.

12. The medication delivery device of claim 9, wherein the processing device is configured to transmit the sensor data to the external device via the wireless link, the transmission of data occurring during real-time data capture by the sensor while medication is delivered to the patient.

13. A system, comprising:
at least one processing device; and
at least one storage medium having encoded thereon executable instructions that, when executed by the at least one processing device, cause the at least one processing device to:
receive sensor data from a sensor, the sensor data comprising a flow of medication from a medication delivery device (MDD) to a patient at a delivery site; and
operate an indicator to indicate that the MDD may be removed from the delivery site when a predetermined amount of time has elapsed after the sensor data that the at least one processing device receives corresponds to a sensed flow rate of medication from the MDD being zero.

14. The system of claim 13, wherein:
the sensor data comprises a flow of medication from the MDD through a cannula of the MDD to the patient at the delivery site; and
the executable instructions, when executed by the at least one processing device, cause the at least one processing device to operate the indicator to indicate that the cannula may be removed from the delivery site when the predetermined amount of time has elapsed after the sensor data that the at least one processing device receives corresponds to the sensed flow rate of medication from the MDD being zero.

15. The system of claim 13, wherein the executable instructions, when executed by the at least one processing device, further cause the at least one processing device to:
analyze the sensed flow rate of medication from the MDD;
determine if a clog is present in the MDD based on the sensed flow rate of medication from the MDD; and
upon determination that the clog is present in the MDD, operate the indicator to indicate the clog is present in the MDD.

16. The system of claim 13, wherein the indicator is positioned on the MDD.

17. A method, comprising:
receiving sensor data from a sensor, the sensor data comprising a flow of medication from a medication delivery device (MDD) to a patient at a delivery site;

determining that the sensor data received from the sensor corresponds to a sensed flow rate of medication from the MDD being zero; and operating an indicator to indicate that the MDD may be removed from the delivery site when a predetermined amount of time has elapsed after the sensor data received from the sensor corresponds to the sensed flow rate of medication from the MDD being zero.

18. The method of claim 17, wherein:

the sensor data comprises a flow of medication from the MDD through a cannula of the MDD to the patient at the delivery site; and the method further comprises operating the indicator to indicate that the cannula may be removed from the delivery site when the predetermined amount of time has elapsed after the sensor data received from the sensor corresponds to the sensed flow rate of medication from the MDD being zero.

19. The method of claim 17, wherein the indicator is positioned on the MDD.

20. The method of claim 17, further comprising:

analyzing the sensed flow rate of medication from the MDD;

determining if a clog is present in the MDD based on the sensed flow rate of medication from the MDD; and upon determination that the clog is present in the MDD, operating the indicator to indicate the clog is present in the MDD.

\* \* \* \* \*